United States Patent
Gmeiner et al.

(10) Patent No.: US 10,791,917 B2
(45) Date of Patent: Oct. 6, 2020

(54) MICRO-OPTICAL SURGICAL PROBES AND MICRO-OPTICAL PROBE TIPS AND METHODS OF MANUFACTURE THEREFOR

(71) Applicant: Synaptive Medical (Barbados) Inc., Toronto (CA)

(72) Inventors: Timotheus Anton Gmeiner, Toronto (CA); Siu Wai Jacky Mak, Toronto (CA); Kresimir Franjic, Toronto (CA)

(73) Assignee: Synaptive Medical (Barbados) Inc., Bridgetown (BB)

( * ) Notice: Subject to any disclaimer, the term of this patent is extended or adjusted under 35 U.S.C. 154(b) by 0 days.

(21) Appl. No.: 16/534,392

(22) Filed: Aug. 7, 2019

(65) Prior Publication Data

US 2020/0029796 A1   Jan. 30, 2020

Related U.S. Application Data

(62) Division of application No. 15/607,853, filed on May 30, 2017, now Pat. No. 10,413,167.

(51) Int. Cl.
*G02B 6/36* (2006.01)
*A61B 1/07* (2006.01)
(Continued)

(52) U.S. Cl.
CPC ............ *A61B 1/07* (2013.01); *A61B 1/00165* (2013.01); *A61B 1/00188* (2013.01); *A61B 1/042* (2013.01); *A61B 1/05* (2013.01); *A61B 1/055* (2013.01); *B33Y 10/00* (2014.12); *B33Y 80/00* (2014.12); *G02B 6/3624* (2013.01); *G02B 23/243* (2013.01); *G02B 23/2423* (2013.01); *G02B 23/2469* (2013.01); *A61B 17/3421* (2013.01); *A61B 2034/2055* (2016.02);
(Continued)

(58) Field of Classification Search
None
See application file for complete search history.

(56) References Cited

U.S. PATENT DOCUMENTS

| 5,891,015 A | 4/1999 | Strahle |
| 5,902,246 A | 5/1999 | McHenry et al. |

(Continued)

FOREIGN PATENT DOCUMENTS

WO    2017/059960 A1    4/2017

OTHER PUBLICATIONS

Search report issued by the Intellectual Property Office of the United Kingdom in relation to corresponding GB Application No. GB1808688.4 dated Nov. 16, 2018, 5 pgs.
(Continued)

*Primary Examiner* — Chad H Smith

(57) ABSTRACT

Described are various embodiments of micro-optical surgical probes and micro-optical probe tips and methods of manufacture therefor. In some embodiments, multichannel micro-optical probe tip structures are directly manufactured upon respective optical channel waveguides, or again manufactured to integrally define respective optical coupling to these waveguides. In some embodiments, micro-optical probe tip structures are manufactured via a 3D laser printing process. Specific embodiments include, but are not limited to, spectroscopic or particularly Raman spectroscopy probes and their associated multichannel probe tip structures, and multichannel endoscopes.

11 Claims, 13 Drawing Sheets

(51) Int. Cl.

| | |
|---|---|
| *G02B 23/24* | (2006.01) |
| *A61B 1/055* | (2006.01) |
| *B33Y 10/00* | (2015.01) |
| *B33Y 80/00* | (2015.01) |
| *A61B 1/00* | (2006.01) |
| *A61B 1/04* | (2006.01) |
| *A61B 1/05* | (2006.01) |
| *G02B 6/24* | (2006.01) |
| *A61B 90/30* | (2016.01) |
| *F21V 8/00* | (2006.01) |
| *A61B 90/00* | (2016.01) |
| *A61B 34/20* | (2016.01) |
| *A61B 17/34* | (2006.01) |

(52) U.S. Cl.
CPC . *A61B 2034/2065* (2016.02); *A61B 2090/306* (2016.02); *A61B 2090/3614* (2016.02); *G02B 6/0008* (2013.01); *G02B 6/24* (2013.01)

(56) References Cited

U.S. PATENT DOCUMENTS

| | | | |
|---|---|---|---|
| 6,006,001 A * | 12/1999 | Alfano | G02B 6/241 |
| | | | 385/115 |
| 6,035,229 A | 3/2000 | Silverstein et al. | |
| 8,389,893 B2 | 3/2013 | Kempe et al. | |
| 8,986,563 B2 | 3/2015 | Thiel et al. | |
| 9,302,430 B2 | 4/2016 | Thiel et al. | |
| 2002/0013513 A1 | 1/2002 | Bala | |
| 2002/0156380 A1 | 10/2002 | Feld et al. | |
| 2005/0283048 A1 | 12/2005 | Gill et al. | |
| 2006/0041193 A1 | 2/2006 | Wright et al. | |
| 2008/0300456 A1 | 12/2008 | Irion et al. | |
| 2013/0150731 A1 | 6/2013 | Chang et al. | |
| 2013/0229651 A1 * | 9/2013 | Ouwerkerk | G01J 3/02 |
| | | | 356/301 |
| 2014/0221740 A1 | 8/2014 | Kawula et al. | |
| 2015/0313471 A1 * | 11/2015 | Dholakia | A61B 5/6852 |
| | | | 600/411 |
| 2016/0041477 A1 | 2/2016 | Hoffmann et al. | |
| 2016/0114530 A1 | 4/2016 | Thiel et al. | |
| 2016/0296104 A1 | 10/2016 | Smith | |
| 2016/0332365 A1 | 11/2016 | Reiner et al. | |

OTHER PUBLICATIONS

Cojoc, "Optical micro-structures fabricated on top of optical fibers by means of two-photon photopolymerization", Microelectronic Engineering, vol. 87, 2009, pp. 876-879.

Giessen, H., Press Release, 3D Printing Enables the Smallest Complex Micro-Objectives, Jun. 2016, 2 pgs.

Gissibl, T. et al., "Two-photon direct laser writing of ultracompact multi-lens objectives", Nature Photonics, vol. 10, Jun. 27, 2016, pp. 554-560.

Gissibl, T. et al., "Sub-micrometre accurate free-form optics by three-dimensional printing on single-mode fibres", Nature Communications, vol. 7, Jun. 24, 2016, pp. 1-9.

Niesler, F. et al., "Two-Photon Polymerization—A Versatile Microfabrication Tool", Laser Technik Journal, vol. 14, Issue 3, Jun. 3, 2017, pp. 44-47.

Ostendorf, A. et al., "Two-Photon Polymerization: A new Approach to Micromachining", Photonics Spectra, Oct. 2006, pp. 1-8.

Thiele, S., et al., "Ultra-compact on-chip LED collimation optics by 3D femtosecond direct laser writing", Optics Letters, vol. 41, No. 13, Jul. 1, 2016, pp. 3029-3032.

* cited by examiner

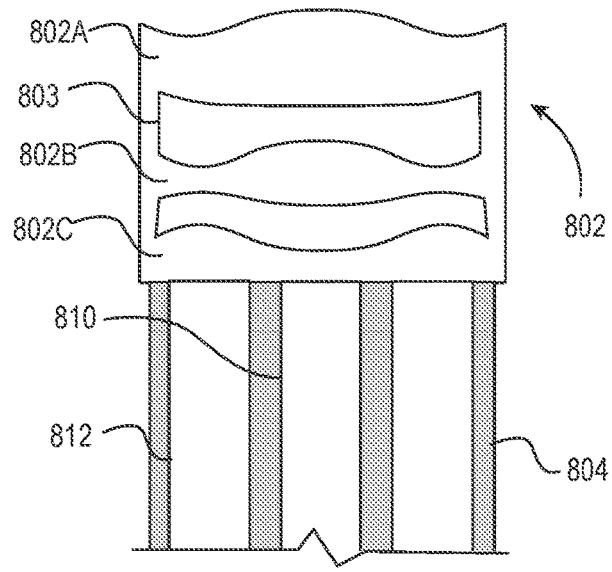
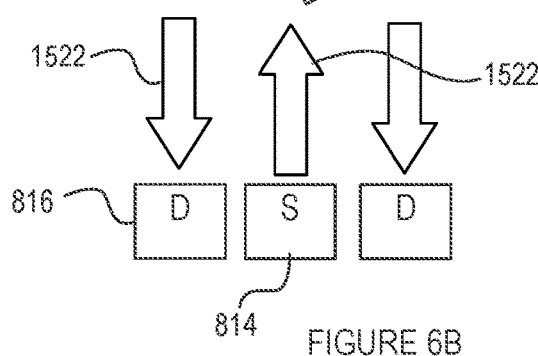
FIGURE 6B
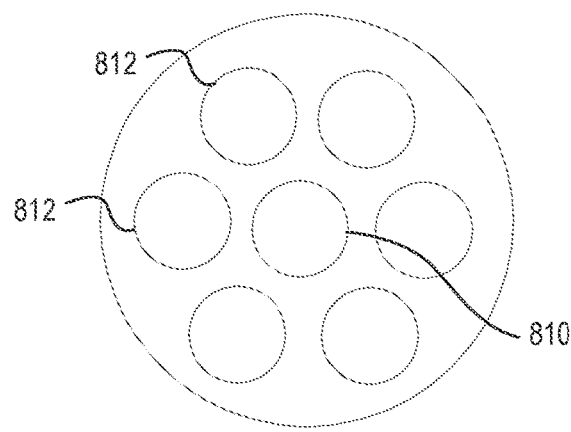
FIGURE 6A
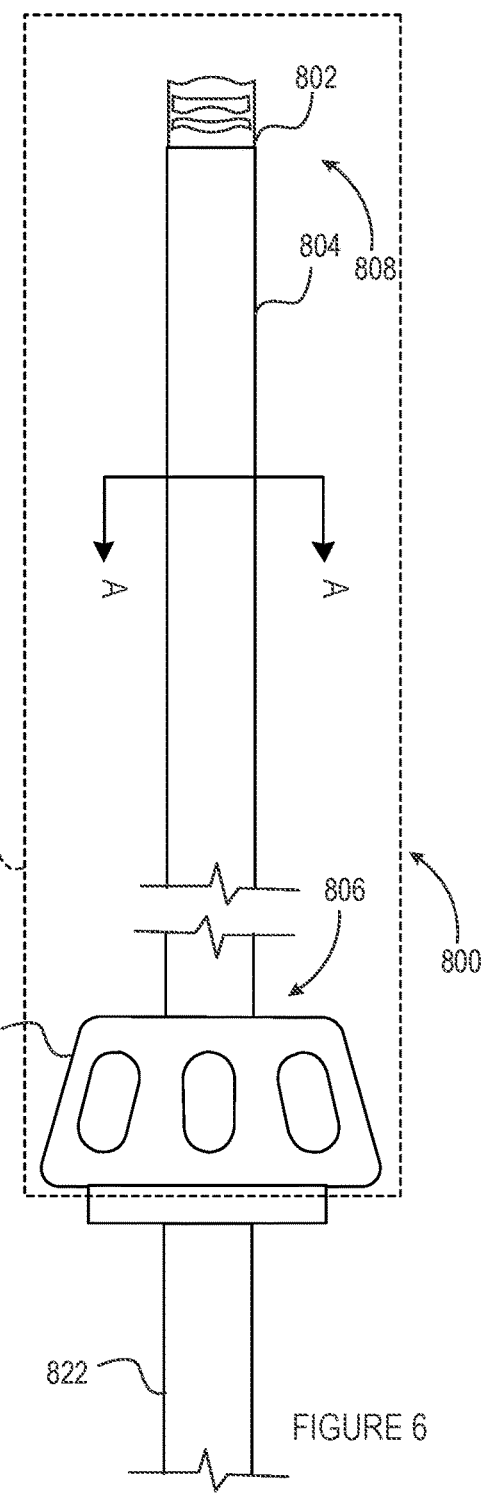
FIGURE 6

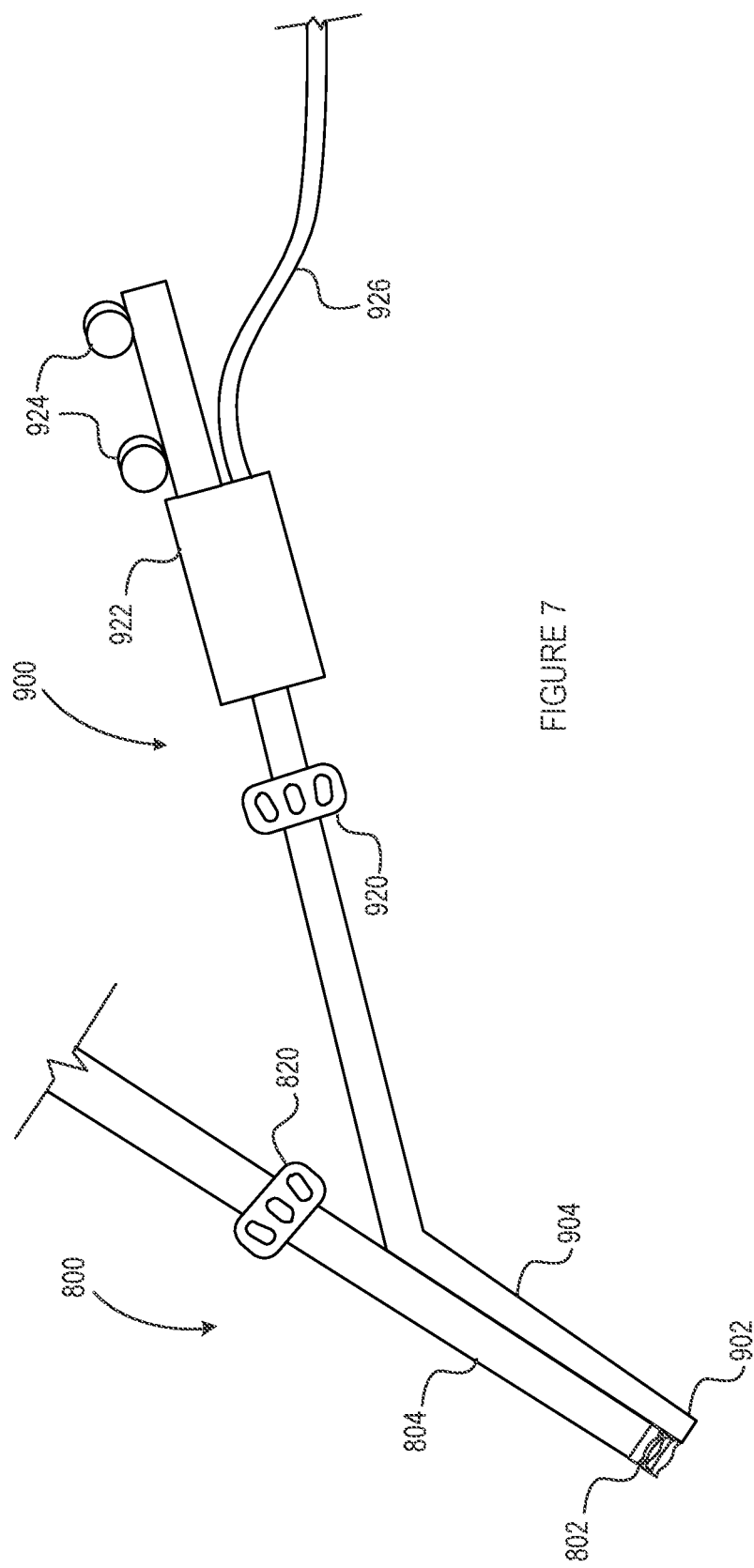

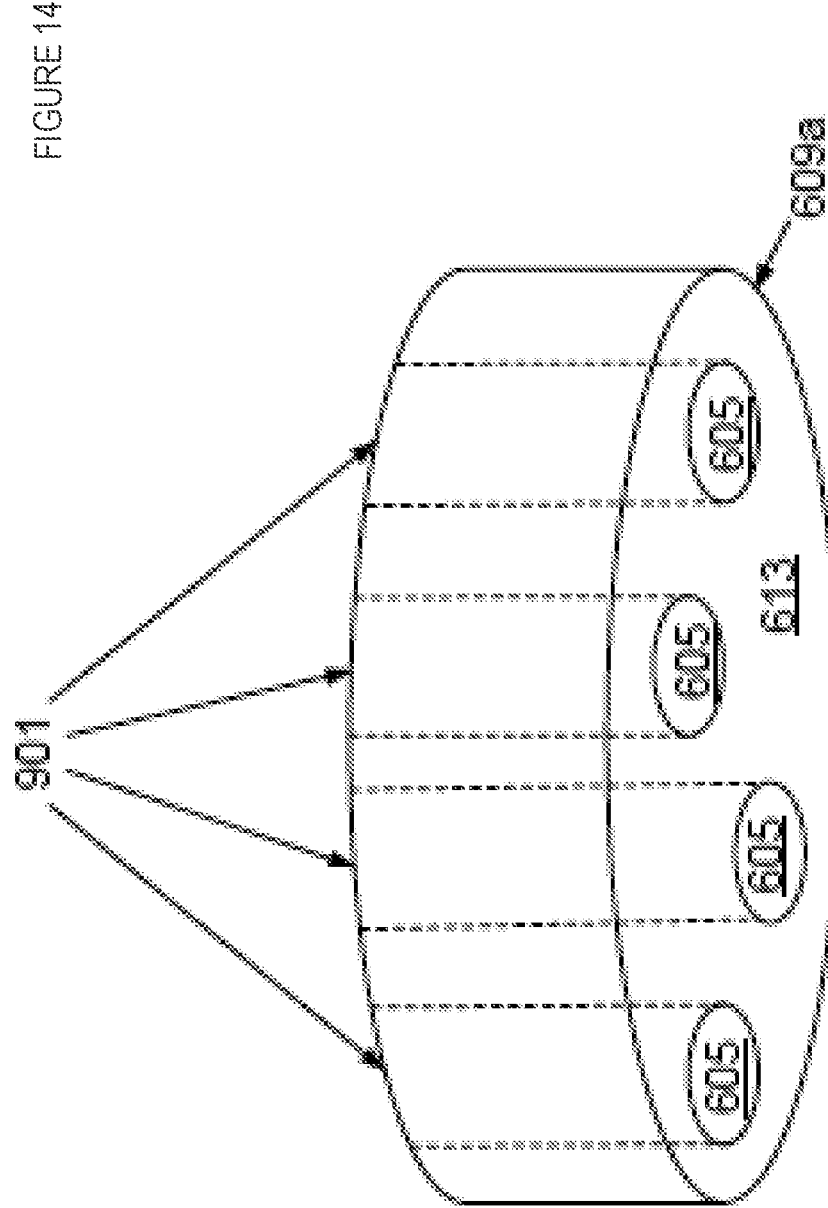

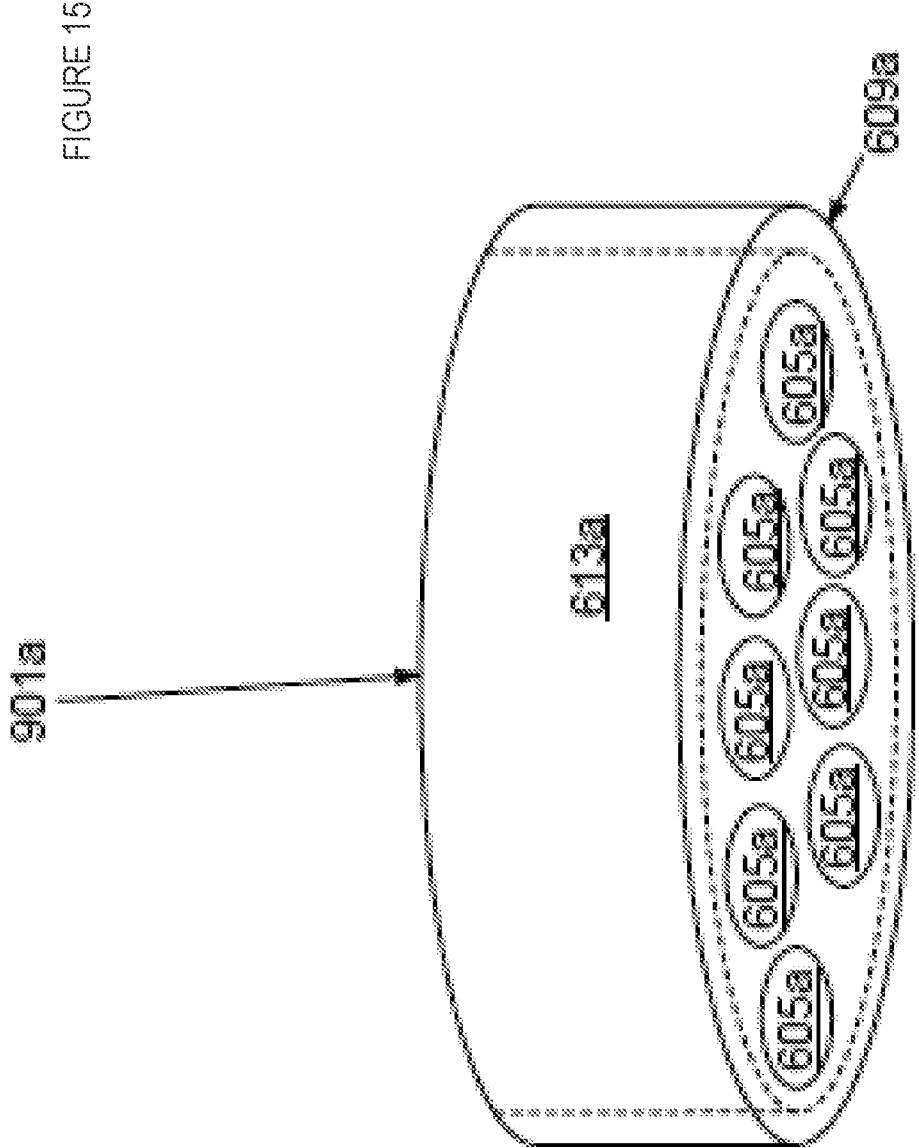

MICRO-OPTICAL SURGICAL PROBES AND MICRO-OPTICAL PROBE TIPS AND METHODS OF MANUFACTURE THEREFOR

FIELD OF THE DISCLOSURE

This application is a divisional of U.S. patent application Ser. No. 15/607,853 filed on May 30, 2017 entitled MICRO-OPTICAL SURGICAL PROBES AND MICRO-OPTICAL PROBE TIPS AND METHODS OF MANUFACTURE THEREFOR, the entire contents of which are hereby incorporated by reference.

The present disclosure relates to medical instruments, tools and systems, and, in particular, to micro-optical surgical probes and micro-optical probe tips and methods of manufacture therefor.

BACKGROUND

Various optical surgical probes, tools and instruments have been developed to improve the accuracy and ultimate success of a given surgical procedure. Known imaging tools for visually closed-access surgical procedures, for example those channelled through an anatomical lumen (e.g. vascular, intestinal procedures), may include fibre optic scopes, optical coherence tomography (OCT) probes, micro ultrasound transducers and the like, wherein a generally flexible tool is inserted and channelled to a surgical site of interest. Similar tools for visually closed-access surgical procedures, for example those introduced within an open cavity such those involved in port-based surgical procedures or the like, may also include fibre optic scopes, in some instances, provided by way of a substantially rigid scope body that can be visually or externally tracked via a procedural imaging and tracking system, for example.

One particular impediment to the development of improved optical surgical tools, particularly as surgical procedures are continuously seeking to reduce or minimize required surgical access areas, is the lack of small-diameter optical probes and their related optical components. This challenge is only compounded for surgical probes involving multiple optical channels and/or paths.

This background information is provided to reveal information believed by the applicant to be of possible relevance. No admission is necessarily intended, nor should be construed, that any of the preceding information constitutes prior art or forms part of the general common knowledge in the relevant art.

SUMMARY

The following presents a simplified summary of the general inventive concept(s) described herein to provide a basic understanding of some aspects of the disclosure. This summary is not an extensive overview of the disclosure. It is not intended to restrict key or critical elements of embodiments of the disclosure or to delineate their scope beyond that which is explicitly or implicitly described by the following description and claims.

A need exists for micro-optical surgical probes and micro-optical probe tips and methods of manufacture therefor, that overcome some of the drawbacks of known techniques, or at least, provides a useful alternative thereto. Some aspects of this disclosure provide examples of such probes, tools and methods.

For instance, in accordance with some aspects of the present disclosure, there is provided a medical probe for internally probing tissue or fluid within a body, the probe comprising: an elongate probe body having an external end, and an insertable end to be inserted within the body toward the tissue or fluid to be probed; an illumination waveguide disposed along the probe body to output optical illumination from the insertable end toward the tissue or fluid to be probed; a collection waveguide disposed along the body to collect, from the insertable end, an optical response of the tissue or fluid to the output optical illumination; and an optical probe tip structure integrally fabricated atop both the illumination waveguide and the collection waveguide to optically relay the output optical illumination from the illumination waveguide and the optical response to the collection waveguide.

In one embodiment, the illumination waveguide is a core illumination waveguide, the collection waveguide comprises a set of circumferentially disposed collection waveguides circumferentially disposed around and parallel to the core illumination waveguide, and the optical probe tip structure is optically fabricated atop and to optically couple with both the core illumination waveguide and the circumferentially disposed collection waveguides.

In one embodiment, the optical response is defined by a designated optical collection spectrum, and the optical probe tip structure further comprises a collection wavelength-selective element defined within a collection optical path of the optical response toward the collection waveguide to at least partially confine the optical response to the designated optical collection spectrum.

In one embodiment, the collection wavelength-selective element comprises an optical coating deposited upon a surface previously fabricated within the optical path.

In one embodiment, the optical illumination is defined by a designed optical illumination spectrum, and the optical probe tip structure further comprises an illumination wavelength-selective element defined within an illumination optical path of the optical illumination from the illumination waveguide to at least partially confine the optical illumination to the designated optical illumination spectrum.

In one embodiment, the illumination wavelength-selective element comprises an optical coating deposited upon a surface previously fabricated within the illumination optical path.

In one embodiment, the optical probe tip structure comprises a monolithic structure fabricated of light-transmissive material and integrally shaped to optically couple to both the illumination waveguide and the collection waveguide and optically relay the optical illumination and optical response therefrom and thereto, respectively.

In one embodiment, the optical probe tip structure is at least partially manufactured by a micro-optical 3D printing process executed to directly manufacture the probe tip structure atop both the optical illumination waveguide and the optical collection waveguide.

In one embodiment, the micro-optical 3D printing process is a two-photon laser 3D printing process.

In one embodiment, the optical probe tip structure further comprises a reflective surface for redirecting at least one of the optical illumination and the optical response.

In one embodiment, the reflective surface comprises a reflective coating disposed on a previously fabricated probe tip surface.

In one embodiment, the optical probe tip structure is at least partially fabricated to define one or more beam shaping elements.

In one embodiment, the beam shaping elements are at least partially defined by a lens grating integrally fabricated within the optical probe tip structure and coupling with at least one of the collection waveguide and the illumination waveguide.

In one embodiment, the beam shaping elements are at least partially defined by a set sequential lens sequentially coupling with at least one of the collection waveguide and the illumination waveguide.

In one embodiment, the optical probe tip structure is fabricated to integrally define respective optical engagement paths for each of the illumination waveguide and the collection waveguide to optimize optical engagement therewith upon fabrication.

In one embodiment, the probe is a disposable probe to be operatively coupled at the external end thereof to a reusable device housing an illumination light source and an optical detector, wherein coupling the external end to the reusable device automatically optically couples the light source to the illumination waveguide and the collection waveguide to the optical sensor.

In one embodiment, a diameter of the probe tip structure is no greater than 2 mm.

In one embodiment, a diameter of the probe tip structure is no greater than 1 mm.

In accordance with other aspects, there is provided a method for manufacturing a medical probe comprising: assembling a multichannel fiber bundle comprising at least two optical fibers associated with distinct optical probe channels; micro-fabricating a common monolithic optical probe tip structure via a 3D laser printing process to concurrently engage and respectively optically couple the optical probe tip structure with a common distal end of each of the at least two optical fibers in ultimately defining respective predesigned optical channel paths within the probe tip structure.

In one embodiment, the micro-fabricating comprises micro-fabricating the structure directly upon the common distal end of the at least two optical fibers.

In one embodiment, the micro-fabricating comprises micro-fabricating respective probe tip ports or waveguides to controllably engage and respectively optically couple the optical probe tip structure with each of the at least two optical fibers.

In one embodiment, the micro-fabricating comprises micro-fabricating a common probe tip port to controllably engage the fiber bundle and respectively optically couple the optical probe tip structure with each of the at least two optical fibers.

In one embodiment, the micro-fabricating comprises micro-fabricating a respective lens element for each of the respective predesigned optical channel paths.

In one embodiment, the at least two optical fibers comprise at least one illumination fiber for operative coupling to an illumination light source in relaying illumination via the probe tip structure, and at least one collection fiber for operative coupling to a detector in collecting light in response to the illumination, wherein the method further comprises: defining one or more wavelength-selective features within the optical probe tip structure to govern a spectral response thereof along a corresponding one of the predesigned optical channel paths.

In one embodiment, the defining comprises depositing a wavelength-selective coating upon a designated probe tip structure surface fabricated to intersect the corresponding one of the predesigned optical channel paths.

In one embodiment, the surface comprises an internal surface.

In one embodiment, the defining comprises integrally fabricating a texturized wavelength-selective surface within the probe tip structure to intersect at least one of the predesigned optical channel paths.

In one embodiment, the micro-fabricating comprises fabricating a beam steering surface within the optical probe tip structure to redirect at least one of the predesigned optical channel paths at an angle relative to the fiber bundle.

In accordance with other aspects, there is provided a medical probe for internally probing tissue or fluid within a body, the probe comprising: an elongate probe body having an external end, and an insertable end to be inserted within the body toward the tissue or fluid to be probed; an illumination waveguide disposed along the probe body to output optical illumination from the insertable end toward the tissue or fluid to be probed; a collection waveguide disposed along the body to collect, from the insertable end, an optical response of the tissue or fluid to the output optical illumination; and a monolithically fabricated multichannel optical probe tip structure fabricated of light-transmissive material and integrally formed to optically engage both the illumination waveguide and the collection waveguide to optically relay the output optical illumination from the illumination waveguide and the optical response to the collection waveguide.

In one embodiment, the monolithically fabricated optical structure is at least partially fabricated via a micro-optical 3D laser printing process.

In one embodiment, the micro-optical 3D laser printing process is directly implemented atop both the optical illumination waveguide and the optical collection waveguide to integrally fabricate the monolithically fabricated optical structure thereon.

In one embodiment, the optical response is defined by a designated optical response spectrum; and wherein the optical probe tip structure further comprises a collection wavelength-selective element defined within the monolithically fabricated optical structure along a collection optical path of the optical response to at least partially confine the optical response within the collection waveguide to the designated optical collection spectrum.

In one embodiment, the collection wavelength-selective element comprises an optical coating deposited upon an internal monolithically fabricated surface.

In one embodiment, the optical illumination is defined by a designed optical illumination spectrum, and the optical probe tip structure further comprises an illumination wavelength-selective element defined within the monolithically fabricated optical structure along an illumination optical path of the optical illumination to at least partially confine the optical illumination within the illumination waveguide to the designated optical illumination collection spectrum.

In one embodiment, the illumination wavelength-selective element comprises an optical coating deposited upon an internal monolithically fabricated surface.

In one embodiment, the illumination waveguide is a core illumination waveguide and wherein the collection waveguide comprises a set of circumferentially disposed collection waveguides circumferentially disposed around and parallel to the core illumination waveguide.

In one embodiment, the monolithically fabricated optical probe tip structure is fabricated to integrally define respective optical engagement ports or waveguides for each of the illumination waveguide and the collection waveguide to optimize optical engagement therewith upon assembly.

In one embodiment, the monolithically fabricated optical probe tip structure defines one or more light shaping elements.

In one embodiment, the one or more light shaping elements are integrally formed to focus the output optical illumination.

In one embodiment, the one or more light shaping elements are integrally formed to collect and focus the optical response into the collection waveguide.

In one embodiment, the monolithically fabricated optical probe tip structure at least partially defines one or more optical steering elements to redirect at least one of the output illumination or the optical response relative to the elongate probe body.

In one embodiment, the one or more optical steering elements comprise a reflective surface for concurrently laterally redirecting the output illumination and the optical response to peripherally probe the tissue or fluid.

In one embodiment, the reflective surface is defined by an integrally formed surface coated with a reflective coating.

In one embodiment, the illumination waveguide and the collection waveguide define a first optical probe; the medical probe further comprises a second optical probe defined by a distinct waveguide disposed along the body to relay or collect secondary light via a distinct optical feature defined within the optical probe tip structure; and the monolithically fabricated optical probe tip structure is further integrally formed to define the distinct optical feature and to optically engage the distinct waveguide.

In one embodiment, the monolithically fabricated optical probe tip structure at least partially defines a first optical steering element to redirect the output illumination and the optical response relative to the elongate probe body in defining a first external optical probe port; and the monolithically fabricated optical probe tip structure at least partially defines a second optical steering element to redirect the secondary light relative to the elongate probe body in defining a second external optical probe port.

In one embodiment, the at least one of the first or second optical steering element comprises a reflective surface defined by an integrally formed surface coated with a reflective coating.

In one embodiment, the probe is a disposable probe to be operatively coupled at the external end thereof to a reusable device housing an illumination light source and an optical detector, wherein coupling the external end to the reusable device automatically optically couples the light source to the illumination waveguide and the collection waveguide to the optical sensor.

In accordance with other aspects, there is provided a surgical device for operating on fluid or tissue within a body, the device comprising: a surgical tool having an elongate tool body and an operable tool tip toward a distal tool end thereof that is insertable within the body to operate on the fluid or tissue; and an optical probe as defined above for concurrently probing the fluid or tissue within the body.

In one embodiment, the surgical tool comprises at least one of a suction tool, a resection tool or a pointing tool.

In one embodiment, the surgical device further comprises a set of fiducial markers externally trackable via an external surgical tracking system.

In accordance with other aspects, there is provided a medical probe for internally probing tissue or fluid within a body, the probe comprising: an elongate probe body having an external end, and an insertable end to be inserted within the body toward the tissue or fluid to be probed; an illumination waveguide disposed along the probe body to output optical illumination from the insertable end toward the tissue or fluid to be probed; an optical sensor disposed at the insertable end to collect therefrom an optical response of the tissue or fluid to the output optical illumination; and a monolithically fabricated multichannel optical probe tip structure fabricated of light-transmissive material and integrally formed to optically engage both the illumination waveguide and the optical sensor to optically relay the output optical illumination from the illumination waveguide and the optical response to the sensor.

In accordance with other aspects, there is provided a medical probe for internally probing tissue or fluid within a body, the probe comprising: an elongate probe body having an external end, and an insertable end to be inserted within the body toward the tissue or fluid to be probed; an illumination system to output optical illumination from the insertable end toward the tissue or fluid to be probed; a multichannel optical sensor disposed to collect, from the insertable end, respective optical channel responses of the tissue or fluid to the output optical illumination; and a monolithically fabricated multichannel optical probe tip structure fabricated of light-transmissive material and integrally formed to optically engage the multichannel sensor to respectively optically relay each of the optical channel response to the multichannel sensor.

In one embodiment, the medical probe further comprises a multichannel optical waveguide disposed along the body to collect, from the insertable end, the respective optical channel responses and relay the optical channel responses to the multichannel sensor; wherein the monolithically fabricated multichannel optical probe tip structure is integrally formed to optically engage the multichannel optical waveguide to respectively optically relay each of the optical channel response along respective waveguide channels to the multichannel sensor.

In one embodiment, the multichannel sensor comprises one of a single multichannel sensor or multiple channel-specific optical sensors.

In accordance with yet another aspect, there is provided a medical probe for internally probing or operating on tissue or fluid within a body, the probe comprising: an elongate probe body having an external end, and an insertable end to be inserted within the body toward the tissue or fluid to be probed or operated on; an illumination waveguide disposed along the probe body to output optical illumination from the insertable end toward the tissue or fluid to be probed or operating on; a hollow collection channel disposed along the probe body and operatively coupled to a suction tool to receive as input at least some of the tissue or fluid probed or operated on; and a monolithically fabricated multifunctional probe tip structure fabricated of light-transmissive material and integrally formed to optically engage the illumination waveguide to optically relay the output optical illumination from the illumination waveguide, and having formed therein a hollow probe tip channel formed to mechanically engage the hollow collection channel to collect at least some of the tissue or fluid probed or operated on.

In one embodiment, the output optical illumination comprises laser ablation illumination.

In one embodiment, the medical probe further comprises a laser light source optically coupling into the illumination waveguide.

In one embodiment, the medical probe further comprises the suction tool.

Other aspects, features and/or advantages will become more apparent upon reading the following non-restrictive description of specific embodiments thereof, given by way of example only with reference to the accompanying drawings.

BRIEF DESCRIPTION OF THE FIGURES

Several embodiments of the present disclosure will be provided, by way of examples only, with reference to the appended drawings, wherein:

FIG. 6 is schematic side view of a multi-channel micro-optical probe, for instance a Raman spectroscopy probe having a multi-channel micro-optical probe tip, in accordance with one embodiment of the present disclosure;

FIG. 6A is a schematic cross-sectional view of the probe of FIG. 6 taken along line A-A;

FIG. 6B is a schematic cross-sectional view of the micro-optical probe tip portion of the probe of FIG. 6, showing an optical interface between excitation and collection fibers thereof, and the multi-channel micro-optical probe tip;

FIG. 7 is a schematic diagram of the probe of FIG. 6 when used in conjunction with a tracked surgical tool, such as a tracked suction tool tracked via a medical navigation system, in accordance with an embodiment of the present disclosure;

FIG. 14 is a perspective diagram of an optical element of the flexible high resolution endoscope of FIG. 13, in accordance with one embodiment of the present disclosure; and FIG. 15 is a perspective diagram of an alternative optical element that can be used with the flexible high resolution endoscope of FIG. 13, in accordance with one embodiment of the present disclosure.

Figure 1:
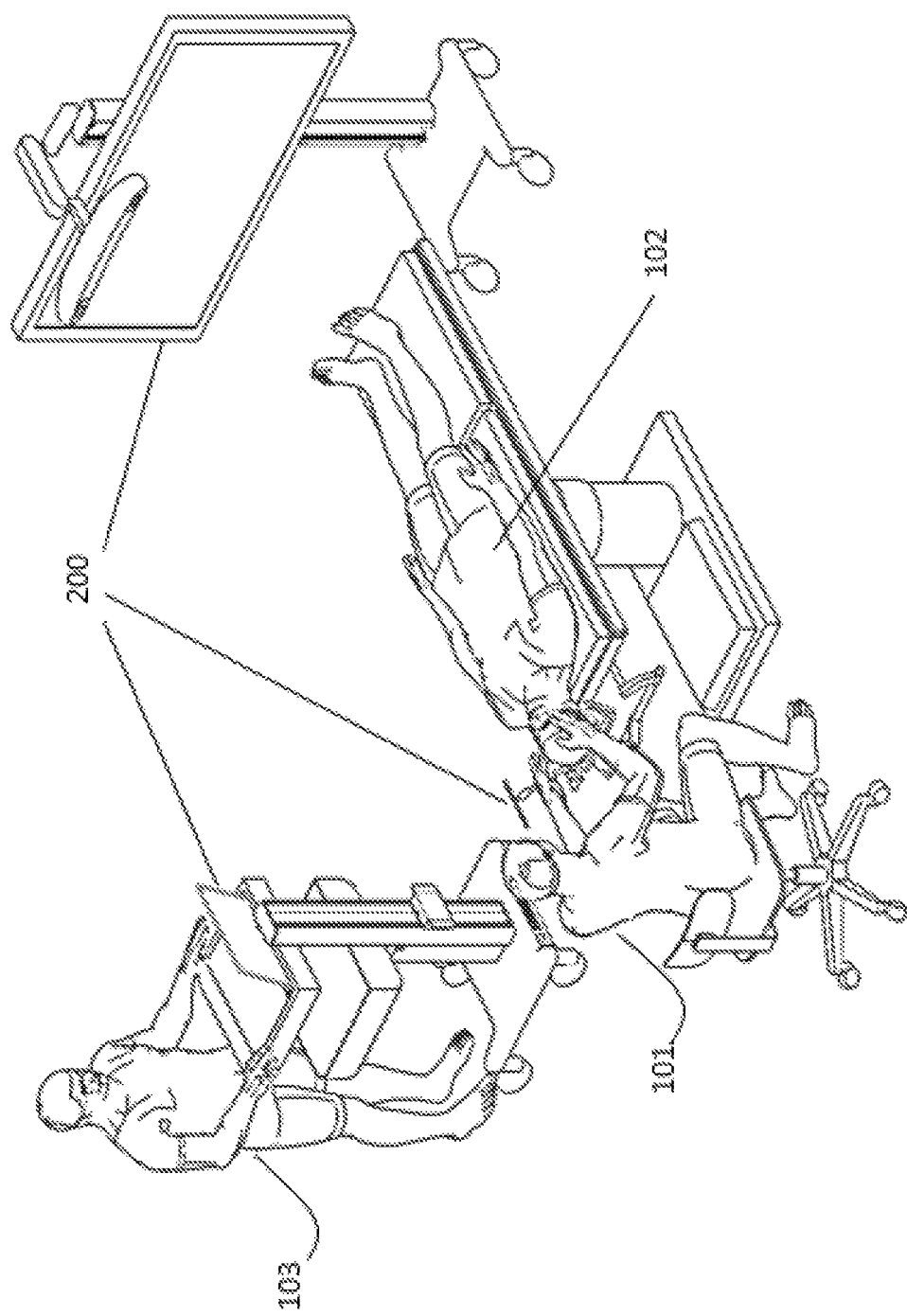
FIG. 1 is a diagram illustrating a perspective view of a medical navigation system, comprising a patient reference device, in an environmental context, such as an operation room, in accordance with an embodiment of the present disclosure.

Elements in the several figures are illustrated for simplicity and clarity and have not necessarily been drawn to scale. For example, the dimensions of some of the elements in the figures may be emphasized relative to other elements for facilitating understanding of the various presently disclosed embodiments. Also, common, but well-understood elements that are useful or necessary in commercially feasible embodiment are often not depicted in order to facilitate a less obstructed view of these various embodiments of the present disclosure.

DETAILED DESCRIPTION

Various implementations and aspects of the specification will be described with reference to details discussed below. The following description and drawings are illustrative of the specification and are not to be construed as limiting the specification. Numerous specific details are described to provide a thorough understanding of various implementations of the present specification. However, in certain instances, well-known or conventional details are not described in order to provide a concise discussion of implementations of the present specification.

The probes, tools, instruments, systems and methods described herein may be useful in the field of neurosurgery, including oncological care, neurodegenerative disease, stroke, brain trauma and orthopedic surgery; however persons of skill will appreciate the ability to extend these concepts to other conditions or fields of medicine. It should be noted that the surgical process is applicable to surgical procedures for brain, spine, knee and any other suitable region of the body.

Various apparatuses and processes will be described below to provide examples of implementations of the system disclosed herein. No implementation described below limits any claimed implementation and any claimed implementations may cover processes or apparatuses that differ from those described below. The claimed implementations are not limited to apparatuses or processes having all of the features of any one apparatus or process described below or to features common to multiple or all of the apparatuses or processes described below. It is possible that an apparatus or process described below is not an implementation of any claimed subject matter.

Furthermore, numerous specific details are set forth in order to provide a thorough understanding of the implementations described herein. However, it will be understood by those skilled in the relevant arts that the implementations described herein may be practiced without these specific details. In other instances, well-known methods, procedures and components have not been described in detail so as not to obscure the implementations described herein.

In this specification, elements may be described as "configured to" perform one or more functions or "configured for" such functions. In general, an element that is configured to perform or configured for performing a function is enabled to perform the function, or is suitable for performing the function, or is adapted to perform the function, or is operable to perform the function, or is otherwise capable of performing the function.

It is understood that for the purpose of this specification, language of "at least one of X, Y, and Z" and "one or more of X, Y and Z" may be construed as X only, Y only, Z only, or any combination of two or more items X, Y, and Z (e.g., XYZ, XY, YZ, ZZ, and the like). Similar logic may be applied for two or more items in any occurrence of "at least one . . . " and "one or more . . . " language.

The embodiments described herein provide different examples of a micro-optical surgical probes and micro-optical probe tips and methods of manufacture therefor that address some of the limitations and impediments of current solutions. For example, in some embodiments, micro-optical probe tips are described for assembly with, or direct manufacture onto distinct waveguides and/or optical tip sensor(s) so to implement spectroscopic and/or multi-channel optical probes amenable for use in a surgical context by virtue of their limited footprint (i.e. millimeter-scale diameter), a characteristic heretofore unavailable using conventional optical manufacturing techniques and thus an impediment to the manufacture, assembly and provision of such micro-optical tools.

For example, in some embodiments, a micro-optical probe tip is manufactured using a 3D printing process (e.g. 3D laser printing or writing) whereby a respective interface for each of the optical probe waveguide, and/or respective optical paths therefor, may be integrally designed and manufactured within the 3D printed tip to promote enhanced optical efficiency and accuracy without unduly impacting an overall operative probe footprint, i.e. probe diameter. Accordingly, in some embodiments, each optical channel path through the common optical probe tip structure can be uniquely and specifically defined to optimize the micro geometry respectively applicable thereto, while optionally further tuning (wavelength specific beam shaping and/or steering, filtering, multiplexing, etc.) each optical path according to particular optical channel requirements or preferences.

In some embodiments, the 3D printed tip may be directly manufactured atop respective optical probe waveguides to enhance optical probe-tip engagement and alignment while also optionally introducing complementary channel-specific beam steering, beam shaping and/or wavelength selective features within the probe tip design and/or at a probe tip/waveguide interface. In other embodiments, the probe tip may be manufactured to manifest channel-specific and/or probe/tip interface characteristics to facilitate probe and channel alignment and interfacing with the probe tip upon assembly. Again, such integrated interfacing features may include, but are not limited to, one or more probe-wide and/or channel-specific beam shaping, beam steering and/or wavelength selective features, as will be detailed further below with reference to the illustrated non-limiting examples provided herewith. In the context of post-fabrication assembly, integrated probe tip design features may, in some embodiments, provide for robust assembly and high-efficiency mating with corresponding channel waveguides, such as with respective fiber optic channels, which may include, but are not limited to, one or illumination waveguides to output optical (e.g. wide spectrum and/or wavelength specific) illumination toward the tissue to be probed; one or more collection waveguides to collect an optical response of the tissue to the output optical illumination; and other output illumination and/or input collection waveguides that may, alone or in combination, achieve a desired or intended optical probe characteristic. In yet other examples, the micro-optical tip structure may also, or alternatively, be manufactured atop or assembled to directly optically couple to a multichannel sensor, for example, whereby respective collection channel optical paths (e.g. different spectral or imaging channels) are directly optically coupled to corresponding channel sensors or channels in a unitary multi-channel sensor. Likewise, a unitary micro-optical probe tip structure may commonly interface with a collection sensor chip-at-the-tip and an illumination waveguide to concurrently and integrally provide multichannel (in/out) functionality. These and other examples will be described in greater detail below.

With reference to FIG. 6, a medical probe 800 having a micro-optical tip 802 will now be described, in accordance with one embodiment. In this embodiment, the medical probe 800 is generally adapted for internally probing tissue or fluid within a body, such as human body, for example, within the context of a surgical procedure (e.g. port-based or lumen based surgical procedure). In the illustrated configuration, the probe 800 comprises an elongate (flexible, rigid or semi-rigid, and optionally disposable or exchangeable) probe body 804 having an external end 806, and an insertable end 808 to be inserted within the body toward the tissue to be probed, in this case, terminated by micro-optical probe tip 802.

As noted above, and with added reference to FIGS. 6A and 6B, the probe 800 consists of a multi-channel optical probe comprising one or more illumination waveguides (e.g. optical fibers) 810 disposed along the probe body 804 to output optical illumination via the probe tip 802, and one or more collection waveguides (e.g. optical fibers or fiber bundles) 812 also disposed along the body 804 to collect, again via the probe tip 802, an optical response of the tissue to the output optical illumination. Generally, the illumination waveguide(s) 810 is optically coupled to a light source 814 (see FIG. 6B), such as a general illumination (e.g. wide spectrum) light source or a wavelength-specific excitation (e.g. laser) light source appropriate for the intended optical probe application. Similarly, the collection waveguide(s) 812 will be optically coupled to one or more respective or joint detectors, sensors and/or optical processing systems 816 (see FIG. 6B) configured to detect and process captured light to render intended results (e.g. optical and/or spectroscopic imaging, characterization and/or diagnostics, etc.). Jointly, and in accordance with some embodiments, the probe 800 may ultimately provide for spectroscopic tissue probing, for example, Raman spectroscopy, whereby an excitation wavelength or wide spectrum probe provided via the illumination waveguide(s) 810 and probe tip 802 triggers an optical response in the probed tissue manifested by a distinct response wavelength and/or spectral profile that can be specifically captured and relayed via the probe tip 802 and collection waveguide(s) 812 for detection and downstream processing, whereby characteristics of the collected light (e.g. absolute or relative amplitude, wavelength, spectral distribution, etc.) provides interpretable information on the probed tissue (e.g. healthy vs. unhealthy tissue, tissue type, tissue damage, etc.).

In some embodiments, the probe 800 may also or alternatively provide for tissue probing using multi-spectral imaging in which a light source illuminates the tissue from the illumination waveguide (e.g. core waveguide 810) while each of the other waveguides 812 collects a respective wavelength/spectrum (i.e. colour) backscattered from the sample.

In yet other embodiments, the probe 800 may further or alternatively provide for tissue probing using fluorescence from the tissue in which one or more probe waveguides illuminate and excite the tissue to generate fluorescence, while one or more other waveguides collect the fluorescence signals.

Other optical tissue characterizations may also readily apply within the present context without departing from the general scope and nature of the present disclosure, as will be understood by the skilled artisan.

In some embodiments, the probe tip 802 will consist of an optical structure integrally fabricated atop the illumination and collection waveguides 810, 812 so to provide and accurately control channel specific interfaces therebetween. For instance, the probe tip 802 may be integrally fabricated, e.g. via a micro-optical 3D printing process or the like (e.g. two-photon laser writing process), as detailed below, directly atop both the illumination waveguide(s) 810 and the collection waveguide(s) 812 to optically relay the output optical illumination from the illumination waveguide(s) 810 and the optical response to the collection waveguide(s) 812. In other embodiments, the probe tip 802 may be separately manufactured, again for example via a micro 3D printing process, for precise alignment and interfacing with respective probe waveguides. These and other examples will be considered in further detail below with reference to further non-limiting examples.

With particular reference to FIG. 6B, the probe tip 802 may comprise one or more beam-shaping structures, integrally formed of sub-structures 802A, B, and C monolithically joined within circumscribing shell 803 in this example, to provide a complex optical structure amenable to relay each optical channel to and from respective waveguides while providing probe-specific and/or channel-specific beam shaping and/or beam steering features/elements, and/or again channel-specific wavelength selective features as will be described in greater detail below with reference to further exemplary embodiments. For instance, by monolithically fabricating complex probe tip structure 802 within circumscribing shell 803, each subcomponent will benefit from inherent axial and lateral alignment (reduce or minimize tilting), while also providing internal protection for the various refractive surfaces defined internally therein while also inherently defining various holes/apertures/cavities therein for use in the subsequent deposition or layering of various coatings, such as channel-specific optical filters and/or wavelength selective coatings, anti-reflective and/or reflective coatings, and the like. For simplicity, the graphical representation of probe tip 802 will be graphically reproduced across multiple embodiments for illustrative purposes, only, with the understanding that different, additional and/or alternative probe tip structures, features and subcomponents may also or alternatively be considered depending on its intended purpose given a particular multi-channel configuration and waveguide interface.

In the configuration shown in FIG. 6A, the illumination waveguide(s) 810 consists of a single optical fiber that is optically coupled at one end to a light source (e.g. laser light source in the context of a Raman probe), whereas the collection waveguide(s) 812 consist of a set of optical fibers laid out in parallel to the illumination fiber 810 and arranged to circumscribe the illumination fiber 810 (e.g. forming a seven-fiber bundle). Each fiber may include a respective sheathing/cladding to enhance optical channel isolation and minimize cross-talk, or again, be embedded or contained within a fiber bundle medium to provide a like effect. Other fiber arrangements and configuration may equally be applicable, as will be appreciated by the skilled artisan. For instance, distinct single channel fibers may be used for illumination and collection purposes, whereas other embodiments may employ two or more such fibers for each or either of illumination and collection. Furthermore, while illustrated fibers are schematically shown to form part of an assembled bundle, separate fibers may also be considered in an unbundled format. Also, while optical fibers are illustrated in this embodiment, other waveguide structures and cross-sections may also be considered depending on the intended optical application at hand and desired result.

In the illustrated embodiment of FIGS. 6, 6A and 6B, the circumferential collection fibers 812 are precisely aligned to integrally and predominantly interface with circumferential optical (e.g. circumferential beam shaping, beam steering and/or wavelength-specific or selective) features of the probe tip 802, whereas the core illumination fiber 810 is precisely aligned to integrally and predominantly interface with core optical (e.g. circumferential beam shaping, beam steering and/or wavelength-specific or selective) features of the probe tip 802, jointly forming a multi-channel (i.e. input/output) probe-tissue interface.

With particular reference to FIG. 6, the probe 800 in this embodiment comprises a disposable or exchangeable probe section 818 whereby the disposable probe body 804 and tip 802 are detachably coupled, e.g. via screw-on or pressure-fitting coupler 820) to reusable probe hardware 822, which for example, may reproducibly interface with probe body optics to relay illumination light from a reusable light (e.g. laser and/or wide spectrum) source and collected light to one or more corresponding detectors and/or optical processing hardware (e.g. spectrometer, optical detector, camera, imaging hardware, etc.). Given the 3D manufacturing process invoked, in some embodiments, to produce the probe tip 802, and the relative affordability of probe body waveguiding optics, disposable probes may be more readily manufactured irrespective of probe tip optic complexity, as compared to using otherwise costly off the shelf probe tip optics, which, in general, are prohibitively large and/or limited for multi-channel applicability and complexity.

In one embodiment, the multi-channel optical probe 800 may be used as a stand-alone device whereby probing functions may be performed alone or in combination with other complementary functions (not shown), for example, in a surgical context in obtaining optical imaging, characterization and/or diagnostic information from probed tissue. As further detailed herein, the probe may be dynamically tracked or monitored via a corresponding surgical navigation system, monitored via one or more optical or surgical tracking tools, or again manually operated and/or tracked via appropriate direct or magnified surgical visualization tools, for example. Likewise, probe outputs may be processed and/or monitored in various forms to provide desired results, such as via graphical or raw data outputs, imaging overlays, indexation and/or annotation, graphical readouts, and the like. These and other such examples will be readily appreciated by the skilled artisan upon reference to the disclosure as a whole.

With added reference to FIG. 7, the probe 800 may also or otherwise be operated in cooperation with one or more complementary tools or instruments 900, for example, where certain complementary features or functions may be leveraged by this tool 900 to avoid hardware duplication and/or reduce an invasive impact of the procedure taking place. In the illustrated example, the complementary tool 900 includes a disposable tool body 904 and tip 902 detachably coupled via screw or pressure-fitting coupler 920 to reusable hardware, in this case comprising an onboard controller 922 (e.g. onboard power source, wireless communication transceiver, operational firmware, drivers, etc.), tracking markers 924 and a tethered link 926 (e.g. suction or resection tool output, wired communication line, power line, etc.). For example, the complementary tool 900 may consist of a tracked suction, imaging and/or resection tool that can work cooperatively with the optical probe 800. For example, the probe 800 may leverage the tool's trackability to provide relative tracking of the optical probe tip 802 and tissue thus probed. Conversely, optical characterization of the optically probed tissue may be used to locate surgical areas or tissue of interest that, once identified, may be immediately removed, for example, via a complementary resection tool 900. Complementary imaging and/or suction functions may equally apply, as will be readily appreciated by the skilled artisan.

Figure 8A:
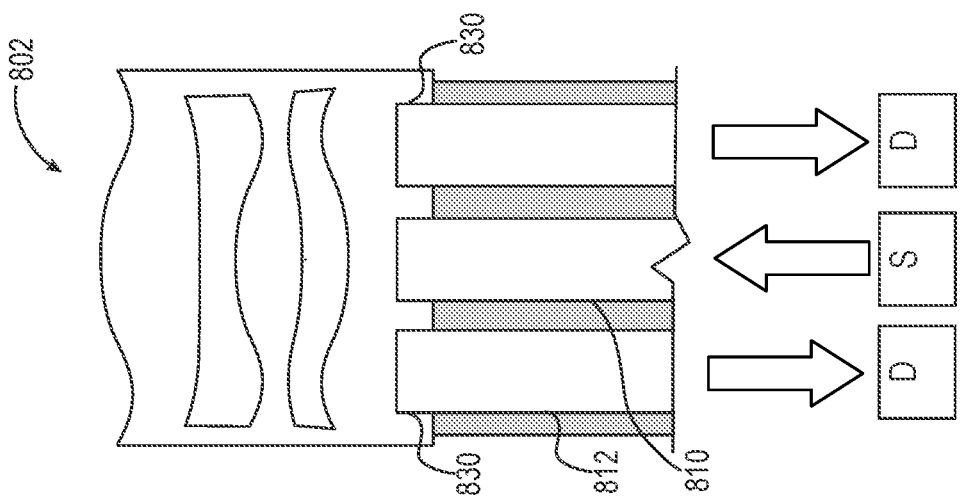
FIGS. 8A to 8C are respective schematic cross-sectional diagrams of alternative optical couplings within a multi-channel micro-optical probe tip, in accordance with different embodiments of the present disclosure.
Figure 8B:
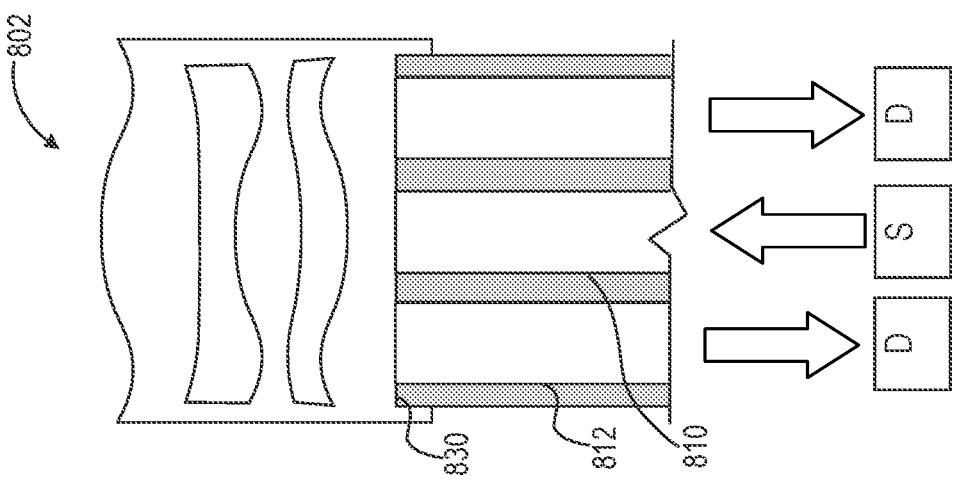
Figure 8C:
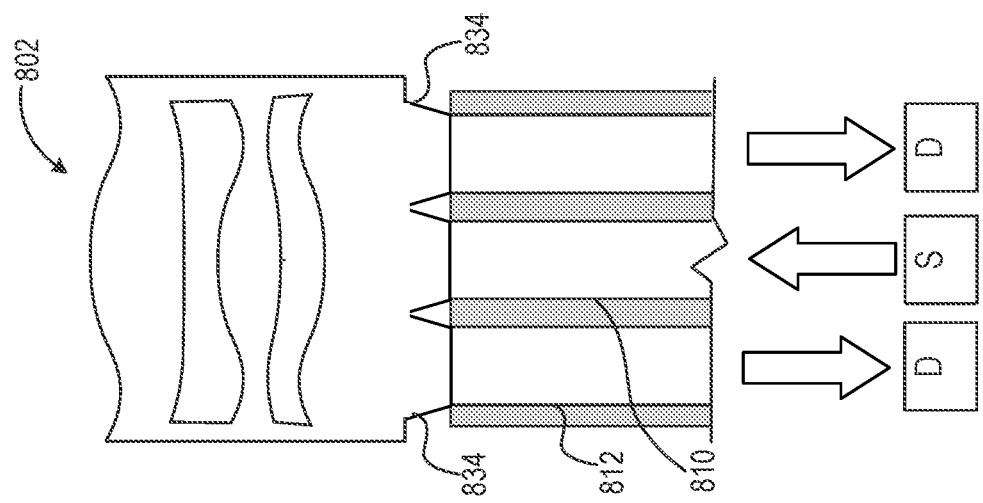

With reference to FIGS. 8A to 8C, different illustrative configurations and arrangements for micro-optical tip 802 are provided, in accordance with different embodiments, as they each interface with distinct illumination and collection waveguides 810 and 812, respectively. As noted above, each of these configurations may be manufactured directly atop channel waveguides, or again manufactured for precision post-fabrication assembly and optical coupling thereto.

In FIG. 8A, the micro-optical probe tip 802 is manufactured to include respective channel ports 830 to receive corresponding channel waveguides therein for mating and precise optical engagement therewith. In doing so, a respective distance between a channel waveguide output and probe tip beam shaping and/or beam steering features can be precisely controlled for optimal performance, and in some embodiments, discretely manufactured to provide distinct channel-specific distances, configurations and/or interfaces.

In comparison, the micro-optical probe tip 802 of FIG. 8B is manufactured to include a common port interface 832, whereby a common port depth and interface for all channels may be precisely defined.

In yet another example, as shown schematically in FIG. 8C, respective waveguide channel interfaces may be discretely manufactured as effective channel waveguide extensions 834 so to precisely control beam shaping and/or beam steering at the interface, for instance, via common or respective waveguide extension lengths, profiles and/or properties.

Figure 9:
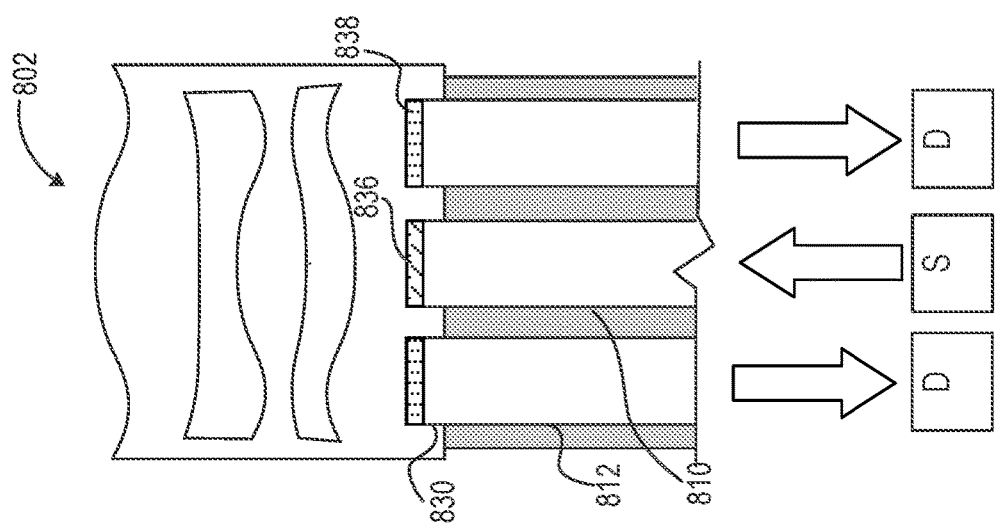
FIGS. 9 is a schematic cross-sectional diagram of a multichannel micro-optical probe tip incorporating respective channel-specific wavelength-selective features, in accordance with one embodiment of the present disclosure.

FIG. 9 provides yet another example of a micro-optical probe tip 802, in this embodiment, encompassing one or more wavelength-selective features integrated therein to further govern optical properties at the probe tip interface with channel waveguides 810, 812. For example, the probe tip 802 shown in FIG. 9 includes respective waveguide channel ports 830 as illustrated in FIG. 8A, but also incudes respective optical filter layers/coatings 836, 838 nested therein, whereby an illumination wavelength output from the illumination waveguide 810 may be precisely selected and controlled by an illumination wavelength-selecting filter 836 (e.g. excitation wavelength in a Raman probe), whereas a collection wavelength input into the collection waveguides 812 may be precisely selected and controlled by a collection wavelength-selecting filter 838 (e.g. collection wavelength in a Raman probe offset from the excitation wavelength).

Figure 10:
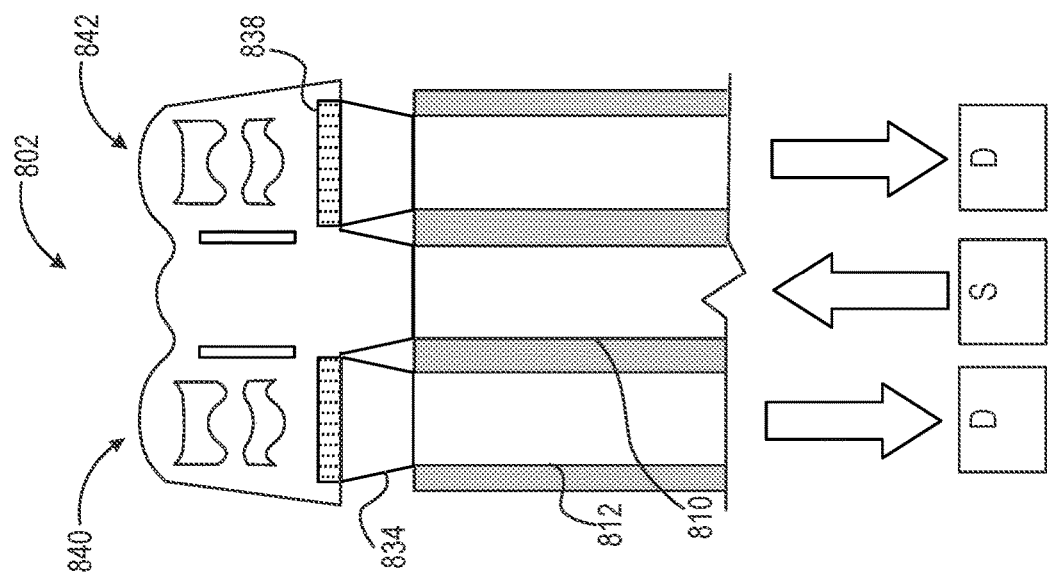
FIG. 10 is a schematic cross-sectional diagram of a multichannel micro-optical probe tip incorporating a channel-specific wavelength-selective feature and respective channel-specific beam shaping features, in accordance with one embodiment of the present disclosure.

Similarly, the micro-optical probe tip 802 of FIG. 10 also includes collection waveguide filters 838, but rather contemplates an embodiment where an illumination wavelength needs not be equally filtered (e.g. within the context of a wavelength specific illumination source such as a laser light source having a sufficiently narrow bandwidth, whereas an offset collection wavelength is still filtered to filter out source wavelength reflections). In the embodiment of FIG. 10, the probe tip 802 reprises the waveguide extensions 834 of FIG. 8C, while embedding collection waveguide filters 838 therewith and providing for distinctly separated illumination and collection beam shaping and/or steering structures (840, 842), nonetheless monolithically manufactured in an integrated micro-optical tip structure. It will be appreciated that the specific features and elements manufactured in each channel-specific micro-optical substructures may vary depending on the application at hand, be they specifically designed and manufactured to focus, diffuse, collimate, project, redirect and/or provide one or more wavelength selective or dispersive functions (e.g. wavelength-specific filter, diffractive element such as structural grating, etc.).

Figure 11:
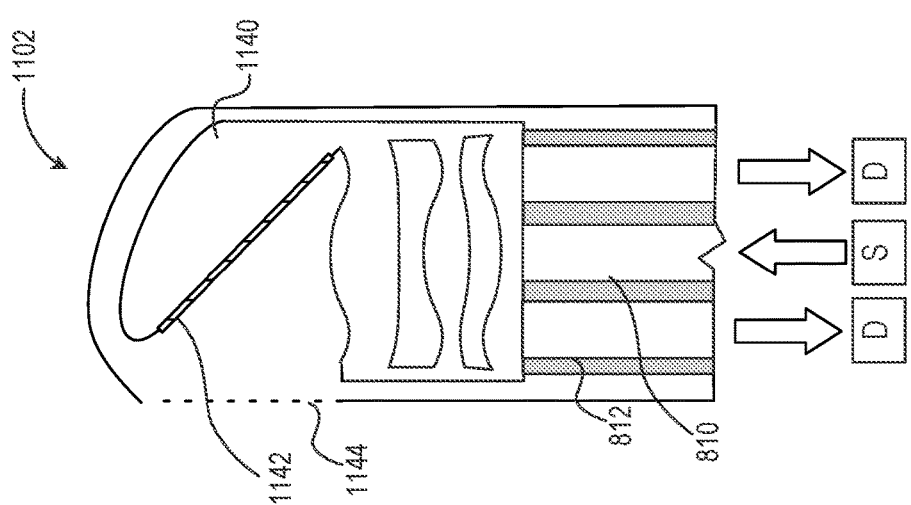
FIG. 11 is a schematic cross-sectional diagram of a multichannel micro-optical probe tip incorporating both beam shaping and beam steering features, in accordance with one embodiment of the present disclosure.

With reference to FIG. 11, and in accordance with yet another embodiment, an alternative micro-optical probe tip 1102, in this embodiment, structurally combining in an integrated structure not only multi-channel beam shaping features as illustratively described above to interface with respective channel waveguides 810, 812, but also a common multichannel beam steering structure 1140 comprising, in this embodiment, a right-angle beam steering structure having a 45-degree internally reflective surface 1142 (e.g. coated or total internal reflective surface) monolithically fabricated within the tip structure 1102 and redirecting light to and from a peripheral window or like aperture 1144. Accordingly, the micro-optical tip structure 1102 provides, within a minimally invasive probe tip structure (e.g. millimeter scale), both multichannel beam shaping and overall optical redirection turning an otherwise axial probe into a radial probe, which provides further intraoperative access to in vivo tissue probing and characterization not only down axis but also around a full periphery of a given surgical access region (i.e. down port periphery in a port-based procedure, peripheral probing within a lumen-based procedure, etc.).

Figure 12:
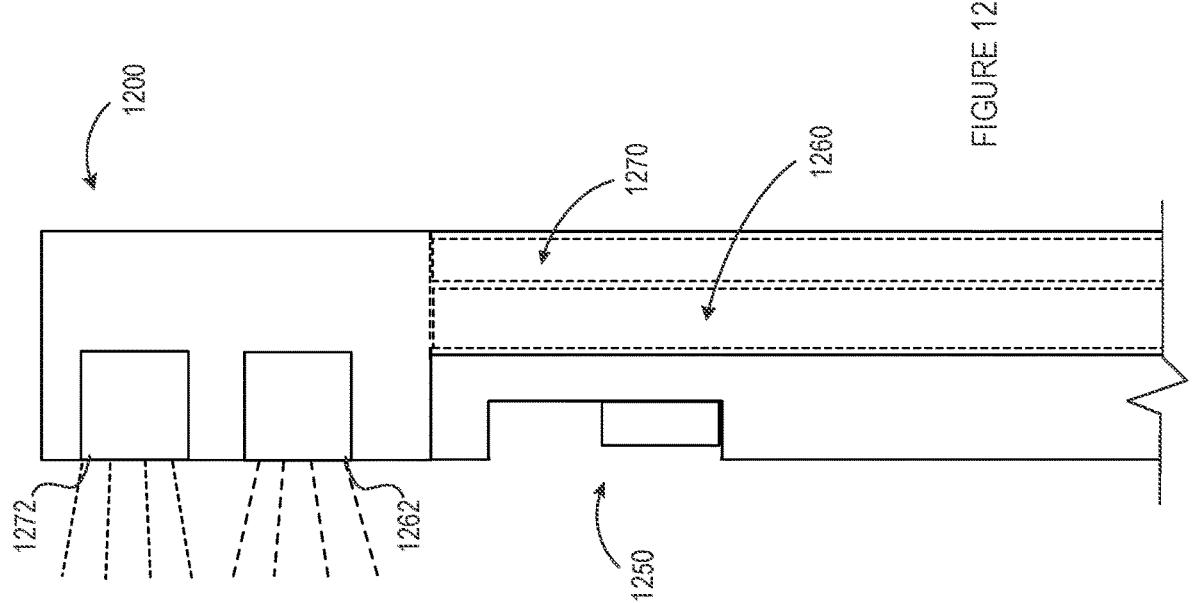
FIG. 12 is a schematic side view of a multifunctional probe tip region cooperatively incorporating a multifunctional micro-optical probe tip, in accordance with one embodiment of the present disclosure.

Expanding from the embodiment illustrated in FIG. 11, FIG. 12 provides a diagrammatical view of a combined multifunctional probe 1200, in this embodiment combining a resection tool 1250, a multichannel (e.g. spectroscopic probe) optical probe 1260 as described above comprising illumination and collection waveguides interfacing with corresponding beam-shaping and/or steering probe tip features (not shown) for optically operating via peripheral window/aperture 1262, and a general imaging probe 1270, for example, providing visible imaging of the surgical site (e.g. relaying images back to an external monitor or scope) via visible imaging window/aperture 1272. Using the micro-optical probe tip manufacturing and interfacing techniques described above, a multifunctional tool, optionally integrated within a singular tool but alternatively commonly addressable via a common tool-probe alignment/attachment such as illustrated for example at FIG. 7, may be used to provide enhanced intra-surgical functions while minimizing tool invasiveness, i.e. by minimizing an overall tool diameter and operational volume requirements.

For example, within the context of an ablation or like tool, an integrated multi-functional micro-fabricated tool tip structure may used to combine an optical output feature shaped and configured to output a desired optical ablation output, with an ablation product collection input for example, operatively coupled to an integrated or cooperatively coupled suction tool. For example, the probe tip optical element can be shaped and configured to interface with an ablation laser source and probe body fiber to shape and direct laser irradiation (e.g. optical beam shaping and/or redirection features, etc.) toward an intra-surgical target. The same micro-fabricated probe tip may also have integrally (e.g. monolithically) fabricated therein one or more hollow tip collection channels (e.g. hollow tube or cylindrical features) shaped and configured to interface with one or more corresponding hollow collection channels (e.g. fibers) disposed along the probe's elongate body, for example, through which suction can be applied from a corresponding suction tool. Accordingly, the micro-fabricated probe tip may include not only optical features (beam shaping, redirecting features and/or wavelength selective features), but also structure features such as holes, cavities and/or channels to concurrently interface with corresponding probe tools to deliver multifunctional features such as suction, resection, ablation or the like.

Figure 13:
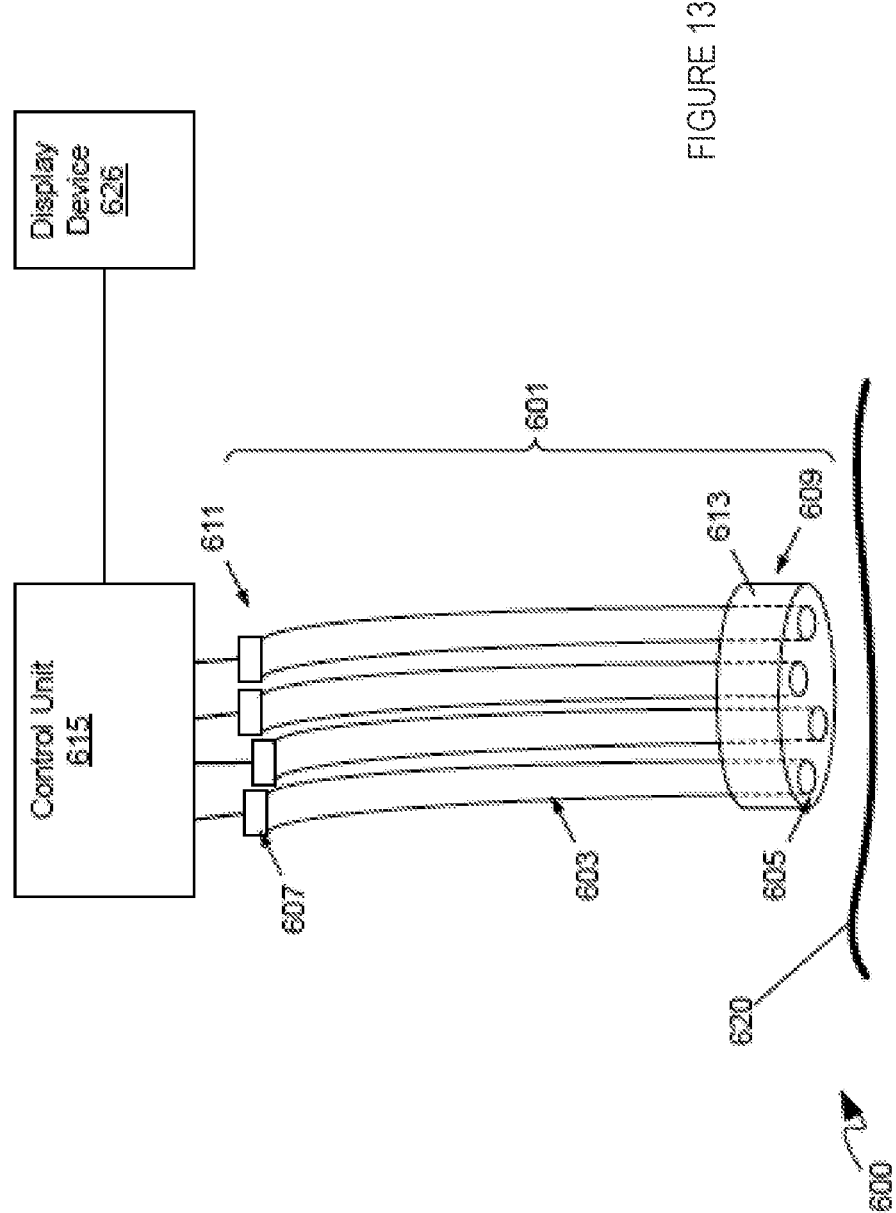
FIG. 13 is a schematic diagram of a system that includes a flexible high resolution endoscope, in accordance with one embodiment of the present disclosure.

With reference now to FIG. 13, and in accordance with yet another embodiment, a schematic diagram is provided of a system 600 that includes an example of a flexible high resolution endoscope 601 that may employ the techniques described herein. It is appreciated that elements of system 600 are not drawn to scale, but are depicted schematically to show functionality.

Endoscope 601 generally comprises: a plurality of optical fibers or fiber bundles 603; a plurality of lenses 605 each integrally formed in a common optical element 613 located at common distal end 609 of the endoscope 601; and, a plurality of cameras 607 at a proximal end 611 of the endoscope 601. In the illustrated embodiment, the lens 605 and cameras 607 are associated in a one-to-one relationship with the plurality of optical fibers/bundles 603, thus allowing each lens 605 to relay light captured thereby toward a corresponding camera 607 via a dedicated intermediary fiber/bundle 603. As above, the common optical element 613 can be manufactured of a 3D printing or like process so to integrally encompass each constituent lens 605 in efficient manner while also encompassing optical/structural features to optimize an alignment of each lens 605 with its corresponding fiber/bundle 603. Likewise, the common optical element 613 may be effectively manufactured directly atop these fibers/bundles 603 to integrally secure proper alignment and optical coupling, while also optionally providing for additional beam forming, steering and/or wavelength specificity.

In general, endoscope 601 is configured to acquire a plurality of images of a tissue sample 620, which can include, but is not limited to, a tissue sample accessible via access port 12 (described below). In particular, respective distal ends 609 of the plurality of optical fibers/bundles 603, and respective lenses 605 located at respective distal ends 609, can be spaced apart from one another to provide different views of objects (such as tissue sample 620) in front of the respective distal ends 609. In some of these implementations endoscope 601 can thereby form a plenoptic camera.

It will be appreciated that endoscope 601 is not limited to four camera, lens and fiber assemblies, but can rather comprise as few as two such assemblies, and can comprise more than four such assemblies, in each configuration allowing for the optional formation of a three-dimensional camera.

As depicted, each lens 605 is integrally formed in a common optical element 613 located at common distal end 609. Common optical element 613 can be manufactured of suitable optical (i.e. light-transmissive) materials, such as those described above as being amenable for 3D printing and manufacturing purposes.

In doing so, the manufactured lens 605 may exhibit different depths of field, different fields of view of objects in front of the plurality of lenses 605, and/or different angular view of objects in front of the plurality of lenses 605, as may be required to achieve a desired effect. Hence, when endoscope 601 is imaging tissue sample 620, tissue sample 620 can be imaged using at least two different depths of field and/or at least two different fields of view and/or at least two different angular views, for example.

Each camera 607 can include, but is not limited to one or more of a charge-coupled device (CCD) camera, a digital camera, an optical camera, and the like, and is generally configured to acquire digital images, and in particular digital images received from a respective lens 605 via a respective optical fiber bundle 603. While not depicted, each camera 607 can further include one or more respective lenses for focusing light from a respective optical fiber 603 onto a respective imaging element (such as a CCD). While not depicted, endoscope 601 can include one or more devices for coupling optical fiber bundles/fibers 603 to a respective camera 607.

Controller 615 can comprise any suitable combination of computing devices, processors, memory devices and the like. In particular, controller 615 can comprise one or more of a data acquisition unit, configured to acquire data and/or images at least from cameras 607, and an image processing unit, configured to process data and/or images from cameras 607 for rendering at display device 626. Hence, controller 615 is interconnected with cameras 607 and display device 626. In some implementations, controller 615 can comprise control and processing unit 300 depicted in FIG. 3, and/or controller 615 can be in communication with control and processing unit 300 depicted in FIG. 3 and/or controller 615 can be under control of communication with control and processing unit 300 depicted in FIG. 3.

In some implementations, however, controller 615 can be a component of endoscope 601 such that endoscope 601 comprises controller 615. In these implementations, endoscope 601 can be provided as a unit with controller 615 which can be interfaced with control and processing unit 300 depicted in FIG. 3, and the like.

Figure 2:
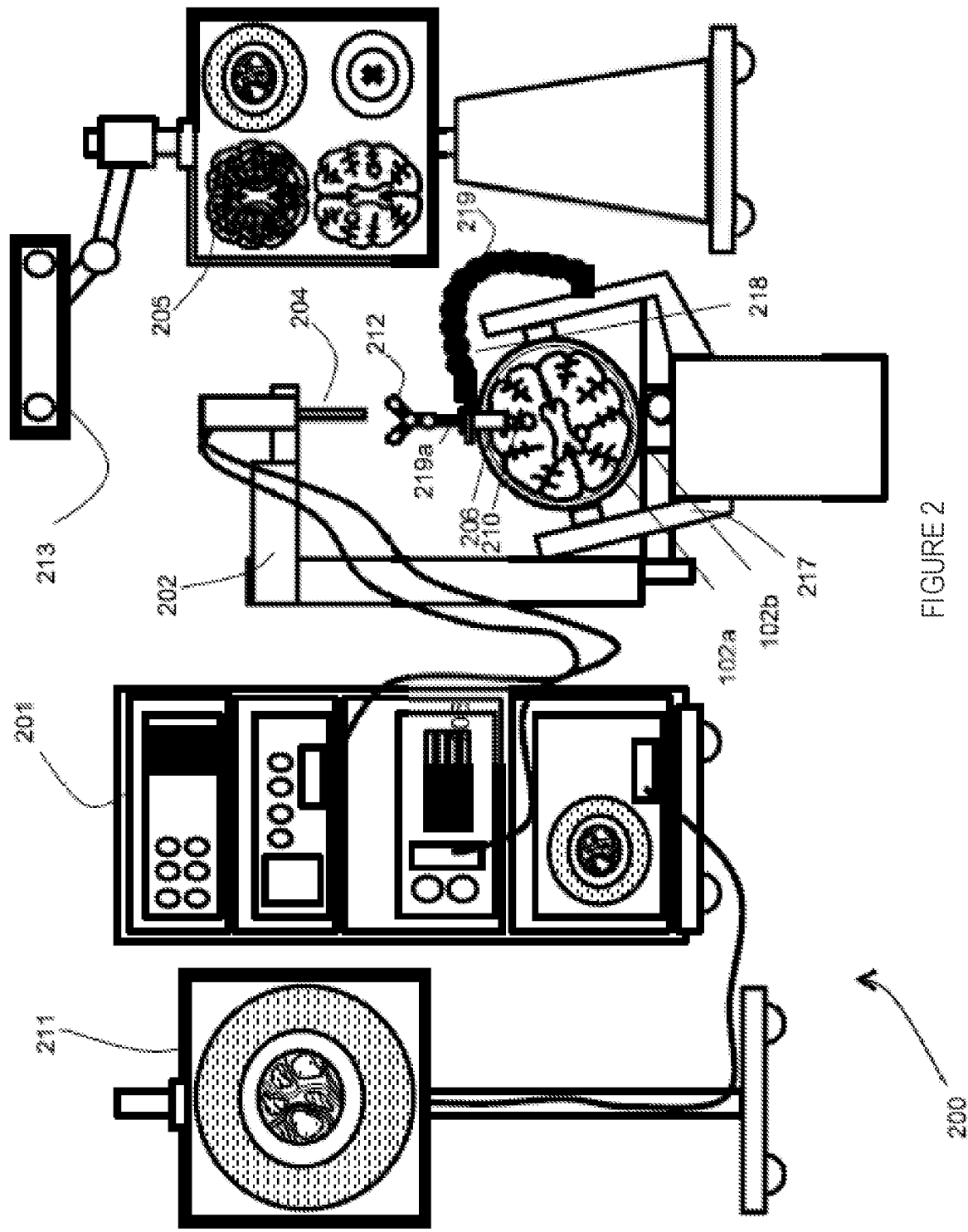
FIG. 2 is a schematic diagram illustrating a medical navigation system, comprising a patient reference device, in accordance with an embodiment of the present disclosure.

Display device 626 can comprise any suitable display device including, but not limited to, cathode ray tubes, flat panel displays, and the like. For example, display device 626 can comprise one or more of monitors 205, 211, as depicted in FIG. 2, and/or displays 305, 311 depicted in FIG. 3.

Further details as to an implementation of the device of FIG. 13, and data captured thereby, can be found in co-pending PCT Application No. PCT/IB2016/054931, the entire contents of which are hereby incorporated herein by reference.

In some embodiments, one or more sensor chips can be provided at the tip of an endoscope (i.e. chip-on-the-tip endoscope) in which electrical cables connect from the distal end of the endoscope to the proximal end to the endoscope controller rather than to relay optical signals thereto via a set of optical fibers/waveguides. For instance, a micro-optical structure as described above could be fabricated directly atop, or to directly interface with the one or more tip sensor chip(s) rather than to optically couple into corresponding waveguides. This approach may improve endoscope robustness by eliminating intermediating waveguides that can get broken from wear and tear while also reducing the endoscope's overall size. Using the probe tip optic design and manufacturing processes described herein, the typically reduced optical quality expected form such design (e.g. distortion, aberration, optical resolution, and stray light) may be circumvented or at least attenuated by providing enhanced tip optics for such chip-on-the-tip implementations. In fact, the same micro-optical tip structure may be designed to improve endoscopic imaging quality while also improving illumination by focusing light relayed by illumination waveguides surrounding the sensor chip.

In some embodiments, a non-symmetrical lens can be designed on a given fiber bundle tip and/or the sensor chip at the tip of the endoscope to optimize imaging angle and spacing for 3D endoscope imaging, for example.

With reference to FIG. 14, common optical element 613 is generally configured to both provide lenses 605 and couple together the plurality of optical fibers/bundles 603 at common distal end 609. Hence, common optical element 613 comprises lenses 605 and, as depicted, respective slots 901 for receiving a respective optical fiber/bundle 603 on a proximal side, each slot 901 in a body of common optical element 613, and each slot 901 terminating at a respective lens 605 at distal end 609. Hence, each slot 901 has a diameter that is similar to a diameter of a respective optical fiber bundle 603 such that each slot 901 can receive a respective optical fiber bundle 603 and seat a distal end of each respective optical fiber bundle 603 at a respective lens 605.

While not depicted, common optical element 613 can further comprise a mechanism for fixing each respective optical fiber/bundle 603 within a respective slot 901; alternatively, adhesives (including, but not limited to optical adhesives) can be used to fix a respective optical fiber bundle 603 within a respective slot 901. In yet another alternative, the common optical element 613 may be directly manufactured atop fibers/bundles 603 in providing direct optical engagement therewith.

Attention is next directed to FIG. 10 which depicts an alternative common optical element 613a, which is substantially similar to optical element 613, with like elements having like numbers, however with an "a" appended thereto. Hence, optical element 613a comprises a plurality of lenses 605a at a distal end 609a. However, in contrast to optical element 613, optical element 613a comprises eight lenses 605a, and one slot 901a configured to receive a plurality of optical fibers/bundles. However, optical element 613a can comprise fewer than eight lenses 605a and more than eight lenses 605a.

Hence, provided herein is a flexible endoscope that comprises multiple optical fibres/bundles, each coupled to an integrated (e.g. monolithically fabricated) multi-lens array at a distal end and multiple cameras at a proximal end. Each lens on the array can convey a separate image to the distal end of each optical fibre bundle and cameras coupled to the proximal end of the optical fibre bundles acquire separate pixelated images. These lower resolution images, acquired by each of the cameras, can be merged and/or combined, and reconstructed using principles of light field imaging and processing, to produce a super-resolution image. This can allow for much higher resolution imaging than with conventional endoscopes, which can allow for better diagnosis and treatment.

Furthermore, using light field processing of the separate images from the cameras, a depth-map of objects imaged by the lenses can be reconstructed, which can allow structures with differing depth to be more easily detected and/or seen. By taking advantage of the underlying optics of the method, omnifocusing (having all object in the scene in-focus), selective post-acquisition focusing, and depth of field control is possible post-acquisition and real-time. This post-processing can allow for removal of "dead" pixels which can be caused by broken fibres within fiber bundles without significant loss of detail As noted above, different manufacturing processes may be invoked to monolithically construct a micro-optical probe tip structure amenable to interfacing with, or being fabricated directly atop or upon, a set of multichannel waveguides, such as illumination and/or collection waveguides, for example, in an in vivo tissue imaging, characterization and/or diagnostic probe, such as an endoscopic and/or spectroscopic probe to name a few examples.

In some embodiments, a 3D laser printing process (interchangeably referred to as a laser writing process or again an additive laser manufacturing process) is invoked to process and progressively fabricate the probe tip structure using transparent materials. For example, one 3D laser printing option includes, but is not limited to, a multiphoton lithography process (see for example, Gissibl et al., Two-photon direct laser writing of ultracompact multi-lens objectives, Nature Photonics 10, 554-560 (2016); Gissibl et al., Sub-micrometre accurate free-form optics by three-dimensional printing on single-mode fibres, Nature Communications 7, Article number: 11763 (2016); Thiele et al., Ultracompact on-chip LED collimation optics by 3D femtosecond direct laser writing, Optics Letters, Vol. 41, No. 13, Jul. 2016, the entire contents of each of which are hereby incorporated herein by reference) in which femtosecond laser pulses can be used to trigger two-photon absorption in highly transparent photoresists to additively realize the monolithic additive fabrication of a micro-optical probe tip design from a single material (e.g. high optical quality photoresist such as IP-S, Nanoscribe GmbH), which may, in some examples, ultimately encompass optical elements at the micro and even nanometer scale.

Accordingly, micro and nano-scale features may be explicitly designed within a singular probe tip structure, as illustratively described above, to produce micro-scale optics integrating particular micro and/or nano-scale beam shaping and/or steering features that, when assembled or built directly atop a set of multichannel waveguides, addresses respective channel optical path requirements. Such designs may be realized and optimized, for example, using available optical design software (e.g. ZEMAX by Zemax, LLC), and exported and converted into a stereolithographic file format to execute the bi-photon lithography using, for example, dip-in direct laser writing using a commercially available femtosecond laser lithography system (e.g. Photonic Professional GT, Nanoscribe GmbH, Germany). Likewise, the introduction of interstitial coatings, layers, textures and/or structures (e.g. non-reflective coatings, reflective coatings, optical filters, gratings, etc., via atomic layer deposition (ALD), micro or nano-patterning/texturizing, etc.) upon and/or between additively fabricated optical features may further enhance multichannel versatility without unduly increasing a form factor of the overall probe tip structure, namely allowing to construct and maintain tip structures having diameters in the order of 1 or 2 mm in some embodiments, or again below 1 mm in some alternative embodiments, or yet again in the order of 0.5 mm in some further alternative embodiments. In yet other embodiments, complex multichannel probe tip structures may be manufactured as described herein to accommodate multichannel bundles having greater diameters, such as 5 mm or even 10 mm. Ultimately, probe tip form factors may be limited or impacted to some extend to the form factors of the waveguides interfacing with the probe tip, rather than by previously prohibitively large probe tip form factors, for instance where a multichannel fiber bundle (e.g. comprising at least two (2) and as many as 4 to 20 or 25 fibers in a millimeter scale probe) may define the ultimate probe tip form factor by virtue of a combined bundle diameter. Accordingly, even when a multichannel probe is combined with other tools in a multifunctional tool design, assembly or set, the overall instrument form factor can be drastically reduced and managed by virtue of the herein described techniques for providing high quality micro-optical probe tips.

As noted above, the solutions described herein are amenable for use in different medical or surgical contexts. However, for the sake of illustration, reference will now be made to a non-limiting example of a port-based neurosurgical system and environment in which the optical probes described herein may be of particular use. It will nonetheless be appreciated by the skilled artisan that this environment is described solely to provide greater context for the embodiments described herein, and that various other surgical or medical environments and systems may equally benefit from the features, functions and advantages provided by the herein-described embodiments.

With reference to FIGS. 1 and 2, and in accordance with one embodiment, an exemplary port-based surgical system and associated tracking/navigation system, incorporating for example a micro-optical probe as described herein, will now be described. As noted above, it will be appreciated that the micro-optical probe described herein within the context of a port-based surgical system may also be amenable to other similar or alternate surgical systems and procedures, and that, without departing from the general scope and nature of the present disclosure. Namely, the utility and applicability of the herein-described probes and tools is not limited to port-based and/or neurological procedures, but rather, may prove particularly useful and desirable in a number of surgical and/or medical environments.

In the illustrated example, the surgical system encompasses an exemplary surgical navigation system 200 operable to track various patient reference devices, in an environmental context, such as an operation room (OR). The system 200 supports, facilitates, and enhances minimally invasive access port-based surgery using a minimally invasive access port-based surgical procedure, though non port-based procedures may equally be considered herein as noted above.

By example only, a surgeon 101 conducts a minimally invasive access port based surgery on a subject, such as a patient 102, in an OR environment. The navigation system 200 generally includes an equipment tower 201, a robotic arm 202 to support an external optical scope 204, and at least one display or monitor 205, 211 for displaying a video image. By example only, an operator 103 is also present to operate, control, and provide assistance for the system 200.

With particular reference to FIG. 2, the equipment tower 201 is generally mountable on a frame, e.g., a rack or a cart, and is configured to accommodate a power supply, e.g., an AC adapter power supply, and at least one computer or controller operable by at least one a set of instructions, storable in relation to at least one non-transitory memory device, corresponding to at least one of surgical planning software, navigation/tracking software, or robotic software for managing at least one of the robotic arm 202 and at least one instrument, such as a surgical instrument, e.g., the access port 206, the introducer 210, and/or one or more other downstream (instrumented) surgical tools (not shown) used during the procedure. For example, the computer comprises at least one of a control unit and a processing unit, such as control and processing unit 400 or 1530 schematically shown in FIGS. 8 and 3, respectively. In the illustrated embodiment, the equipment tower 201 comprises a single tower configured to facilitate coupling of the at least one display device. e.g., a primary display device 211 and a secondary display device 205, with the at least one piece of equipment. However, other configurations are also encompassed by the present disclosure, such as the equipment tower 201 comprising dual towers configured to facilitate coupling of a single display, etc. The equipment tower 201 is also configurable to accommodate an uninterruptible power supply (UPS) for providing emergency power.

To maintain constant positioning of the patient's anatomy of interest during a given procedure, the patient's anatomy may be held in place by a holder appropriate for the procedure in question. For example, in a port-based neurosurgical procedure, such as that illustrated in FIG. 2, a patient's head can be retained by a head holder 217. A craniotomy is performed, a dura flap is formed and retracted, and the access port 206 and introducer 210 can then be inserted into the patient's brain 102b, and the planed procedure is executed while the patient's head remains effectively immobile.

The system also includes a tracking system 213 that is generally configured to track at least one instrument, such as a surgical instrument, tool and/or probe. In FIGS. 1 and 2, the tracking system is initially utilized to track the access port 206 and introducer 210 while the access port is being introduced within the patient's brain so to ultimately locate and define the surgical site and surrounding surgical cavity. However, other intra-operative surgical tools, such as, but not limited to, inner-cavity pointing tools, suction tools, tissue probes (e.g. Raman probes, OCT probes, spectroscopic probes, endoscopes, etc.), resection tools and the like, are also advantageously tracked, alone or in combination, by the tracking system to enhance accuracy and precision of executed operative procedures. Instrument tracking can thus significantly assist the surgeon 101 during the minimally invasive access port-based surgical procedure (or like procedures) both in guiding and confirming procedural actions, but also in aligning real-time surgical cavity imaging, probing and characterization, as detailed below within the context of micro-optical surgical probes, with pre-operative imaging data and intra-operative external imaging (e.g. captured via external optical scope 204 and/or other cameras discussed below). Accordingly, tracking instruments/tools as noted above can significantly benefit enhanced or complementary inner-cavity imaging, localization, characterization and/or mapping.

Accordingly, the tracking system 213 is configured to track and determine, e.g., in real-time by way of a set of instructions corresponding to tracking software and storable in relation to at least one non-transitory memory device, the location of the one or more tracked instruments during the surgical procedure, while also generally tracking a position of the robotic arm 202.

In the illustrated embodiment, the tracking system 213 generally comprises at least one sensor (not shown) for detecting at least one fiducial marker 212 disposable in relation the one or more OR items (e.g. surgical arm 202) and/or surgical instruments (introducer 210) to be tracked. In one example, the tracking system 213 comprises a three-dimensional (3D) optical tracking stereo camera, such as a Northern Digital Imaging® (NDI) optical tracking stereo camera, which can be configured to locate reflective sphere tracking markers 212 in 3D space. In another example, the tracking camera 213 may be a magnetic camera, such as a field transmitter, where receiver coils are used to locate objects in 3D space, as is also known in the art. Accordingly, location data of the mechanical arm 202, access port 206, introducer 210 and and/or other tracked instruments/tools, may be determined by the tracking camera 213 by automated detection of tracking markers 212 placed on these tools, wherein the 3D position and orientation of these tools can be effectively inferred and tracked by tracking software from the respective position of the tracked markers 212.

In the illustrated embodiment of FIG. 2, the secondary display 205 provides an output of the tracking camera 213, which may include, but is not limited to, axial, sagittal and/or coronal views as part of a multi-view display, for example, and/or other views as may be appropriate, such as views oriented relative to the at least one tracked instrument (e.g. perpendicular to a tool tip, in-plane of a tool shaft, etc.). These and other views may be considered in various single or multi-view combinations, without departing from the general scope and nature of the present disclosure.

Still referring to FIG. 2, minimally invasive brain surgery using access ports is a recent method of performing surgery on brain tumors. In order to introduce an access port 206 into a brain, such as the patient's brain 102b, of a patient head's 102a, an introducer, e.g., the introducer 210, comprises an atraumatic tip disposable within the access port 206 to facilitate positioning the access port 206 within the patient brain 102b. As noted above, the introducer 210 further comprises at least one fiducial marker 212 for facilitating tracking by the tracking system 213. Generally, tracked tools such as introducer 210 will include a plurality of fiducial markers to enhance trackability in 3D space.

After the introducer 210 and the access port 206 are inserted into the brain 102b, the introducer 210 is removed to facilitate access to the tissue of the brain 102b through the central opening of the access port 206. However, after the introducer 210 is removed, the access port 206 is no longer being tracked by the tracking system 213.

However, the access port 206 is indirectly trackable by way of additional pointing tools (not shown) configured for identification by the navigation system 200.

In the illustrated embodiment of FIG. 2, the navigation system 200 further comprises a guide clamp 218 for retaining the access port 206. The guide clamp 218 is configured to optionally engage and disengage the access port 206, eliminating the need to remove the access port 206 from the patient 102. In some embodiments, the access port 206 is configured to slide up and down within the guide clamp 218 in a closed position. The guide clamp 218 further comprises a locking mechanism (not shown), the locking mechanism being attachable or integrable in relation to the guide clamp 218, and the locking mechanism being optionally manually actuable, e.g., using one hand as further below described.

The navigation system 200 further comprises an articulating arm 219, such as a small articulating arm, configured to couple with the guide clamp 218. The articulating arm 219 comprises up to six (6) degrees of freedom for facilitating positioning of the guide clamp 218. The articulating arm 219 is attachable at a location in relation to the head holder 217, or in relation to any other suitable patient support structure, to ensure, when locked in place, that the guide clamp 218 is fixed in relation to the patient's head 102a. The articulating arm 219 comprises an interface 219a disposable in relation to the guide clamp 218, wherein the interface 219a is at least one of flexible or lockable into place. Flexibility of the interface 219a facilitates movability of the access port 206 into various positions within the brain 102b, yet still maintains rotatability about a fixed point.

The navigation system 200 may further or alternatively comprise a plurality of wide-field cameras, e.g., two additional wide-field cameras (not shown) being implemented with video overlay information, wherein one camera is mountable in relation to the optical scope 204 and the other camera is mountable in relation to the navigation system 213 (i.e. within the context of an electromagnetic tracking system). In the case of the navigation system 213 comprising an optical tracking device, a video image can be directly extracted therefrom. Video overlay information can then be used to enhance available intra-operative information, for example, by providing an image displaying a physical space and confirming tracking system registration alignment and optional corresponding text and/or indicia, an image displaying a motion range of the robotic arm 202 holding the optical scope 204 and optional corresponding text and/or indicia, and/or an image displaying a guide head positioning and a patient positioning and optional corresponding text and/or indicia.

Other image overlays, as will be described in greater detail below, may further include intraoperative cavity imaging and/or characterization data (e.g. colour mapping, partial image transparency overlay, text and/or indicia), such as provided by a micro-optical probe as described herein. Using such real-time intraoperative inner cavity imaging and characterization data may not only enhance other intraoperative images, such as those rendered by overhead scopes and/or cameras, but also seamlessly integrate with pre-operative images and/or data, for instance, acquired pre-operatively using one more imaging techniques. Accordingly, the surgeon and/or other surgical equipment operator can execute procedures and/or actions with greater clarity, certainty and visibility, thus leading to improved outcomes and risk reduction.

Figure 4:
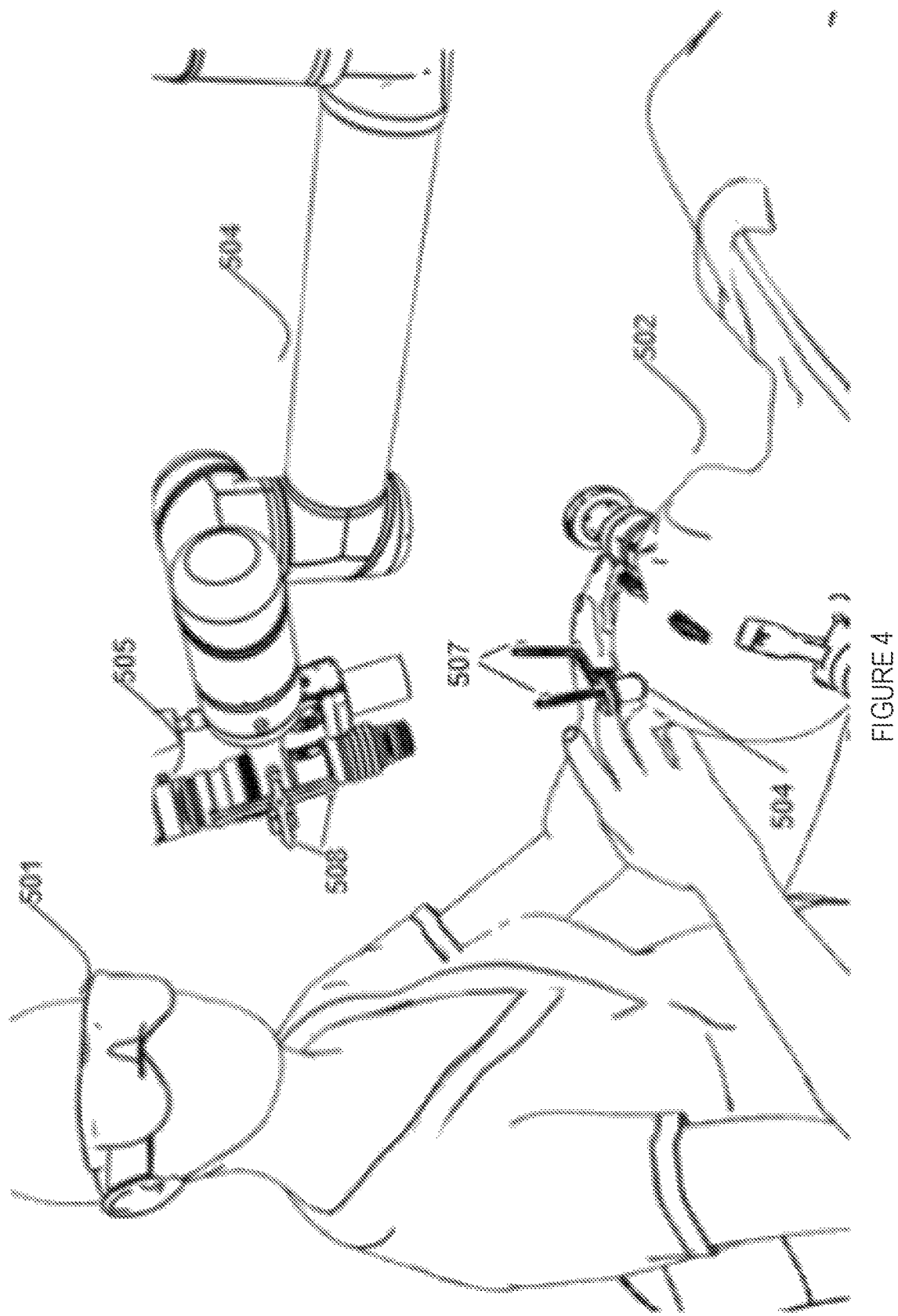
FIG. 4 is a diagram illustrating an access port-based surgical procedure being conducted by way of a navigation system, in accordance with one embodiment of the present disclosure.

With reference to FIG. 4, a diagram of an access port-based surgical procedure conducted by way of the navigation system 200 is illustrated, in accordance with some embodiments of the present disclosure. In this example, a surgeon 501 is resecting a tumor from the brain of a patient 502 through an access port 504. An external scope 505 is coupled with a robotic arm 504, and is used to view down port 504 at a sufficient magnification to allow for enhanced visibility down port 504. The output of external scope 505 is rendered on a visual display.

Figure 5:
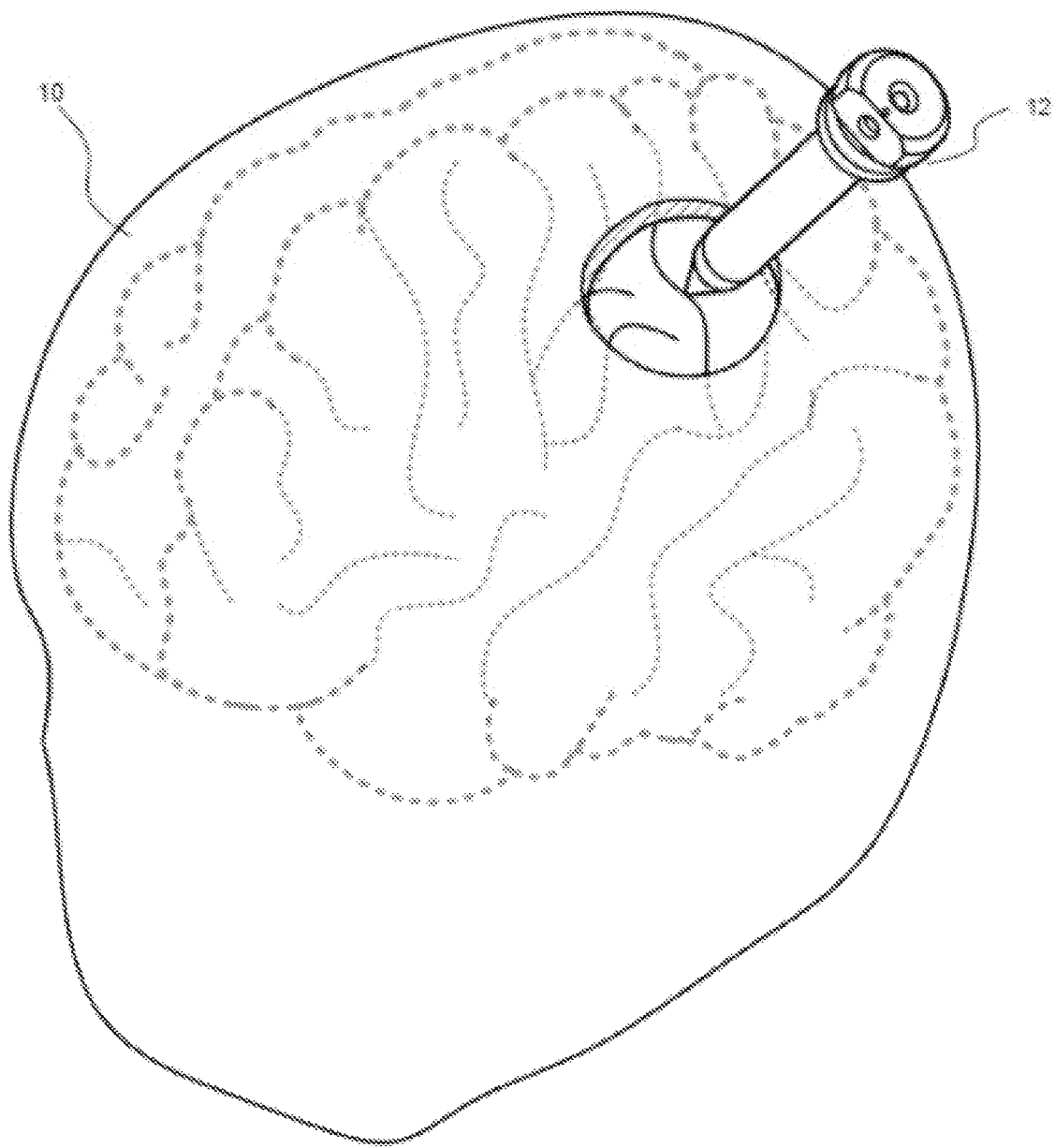
FIG. 5 is a diagram of an access port into a human brain, for providing access to interior brain tissue during a medical procedure, in accordance with one embodiment of the present disclosure.

As introduced above, the procedure illustrated in FIG. 5 may involve disposing active or passive fiduciary markers, respectively, 507, 508, e.g., spherical markers, in relation to at least one of the access port 504 or the external scope 505 for facilitating their tracking (location of these tools) by the tracking system (e.g. tracking system 213 of FIG. 2). The active or passive fiduciary markers, 507, 508, are sensed by sensors of the tracking system 213, whereby identifiable points are provided. A tracked instrument is typically indicated by sensing a grouping of active or passive fiduciary markers, 507, 508, whereby a rigid body, such as a tool or probe, is identified by the tracking system 213, and whereby the position and orientation in 3D of a tracked instrument, such as a tool or probe, is determinable. Namely, a substantially rigid tool can be tracked in 3D space to effectively locate and orient the tool and its various segments and constituent components, provided such segments/components are previously defined and stored against the tracked tool type. Accordingly, a tracked tool may invoke not only general tracking, but also tracking, for example, of the tool's tip or body, and any sensors or probes, as will be detailed below, that may be operatively coupled thereto or utilized therewith in a designated configuration (e.g. at or near a tool tip, angled relative to a tool tip or shaft, displaced and/or angled relative to other tool-mounted sensors, etc.). Typically, a minimum of three active or passive fiduciary markers, 507, 508, are placed on a tracked tool to define the instrument. In the several figures included herewith, four active or passive fiduciary markers, 507, 508, are used to track each tool, by example only.

In one particular example, the fiduciary markers comprise reflectosphere markers in combination with an optical tracking system to determine spatial positioning of the surgical instruments within the operating field. The spatial position of automated mechanical arm(s) or robotic arm(s) used during surgery may also be tracked in a similar manner. Differentiation of the types of tools and targets and their corresponding virtual geometrically accurate volumes can be determined by the specific orientation of the reflectospheres relative to one another giving each virtual object an individual identity within the navigation system. The individual identifiers can relay information to the system as to the size and virtual shape of the tool within the system. The identifier can also provide information such as the tool's central point, the tools' central axis, the tool's tip, etc. The virtual tool may also be determinable from a database of tools provided to the navigation system 200. The marker positions can be tracked relative to an object in the operating room such as the patient. Other types of markers that can be used may include, but are not limited to, radio frequency (RF), electromagnetic (EM), pulsed and un-pulsed light-emitting diodes (LED), glass spheres, reflective stickers, unique structures and patterns, wherein the RF and EM would have specific signatures for the specific tools to which they would be attached. The reflective stickers, structures, and patterns, glass spheres, LEDs could all be detected using optical detectors, while RF and EM could be detected using antennas. Advantages to using EM and RF tags may include removal of the line of sight condition during the operation, where using the optical system removes the additional noise from electrical emission and detection systems.

In a further embodiment, printed or 3D design markers can be used for detection by an auxiliary camera and/or external scope. The printed markers can also be used as a calibration pattern to provide distance information (3D) to the optical detector. These identification markers may include designs such as concentric circles with different ring spacing, and/or different types of bar codes. Furthermore, in addition to using markers, the contours of known objects (e.g., side of the port, top ring of the port, shaft of pointer tool, etc.) can be made recognizable by the optical imaging devices through the tracking system 213. Similarly, or in addition thereto, structural information relating to each tool (size, dimensions, distance and geometric orientation relative to markers) may be used to extrapolate the position and orientation various tool segments, such as the tool tip, and various sensors that may be operatively mounted thereon or associated therewith, as noted above.

As will be appreciated by the skilled artisan, while the above lists a number of tracking techniques and related marker types, other known and future techniques may also be considered within the present context to support and enhance operation of the tracked surgical tools, i.e. optical probes and associated tools, described herein. Namely, the tracking technique for each instrument will generally allow for the tracking of the instrument's position and orientation within a given frame of reference, in which the position and orientation can be tracked, relayed and/or rendered on the surgical system's one or more displays to visually locate the tool, or data/images acquired thereby, within the context of the procedure taking place and/or any otherwise available pre-operative and/or intraoperative images/details.

FIG. 5 illustrates the insertion of an access port 12 into a human brain 10, in order to provide access to interior brain tissue during a medical procedure. In FIG. 5, access port 12 is inserted into a human brain 10, providing access to interior brain tissue. Access port 12 may include, but is not limited to, instruments such as catheters, surgical probes, and/or cylindrical ports such as the NICO BrainPath. Surgical tools and instruments may then be inserted within a lumen of the access port 12 in order to perform surgical, diagnostic or therapeutic procedures, such as resecting tumors as necessary. However, the present specification applies equally well to catheters, DBS needles, a biopsy procedure, and also to biopsies and/or catheters in other medical procedures performed on other parts of the body.

Figure 3:
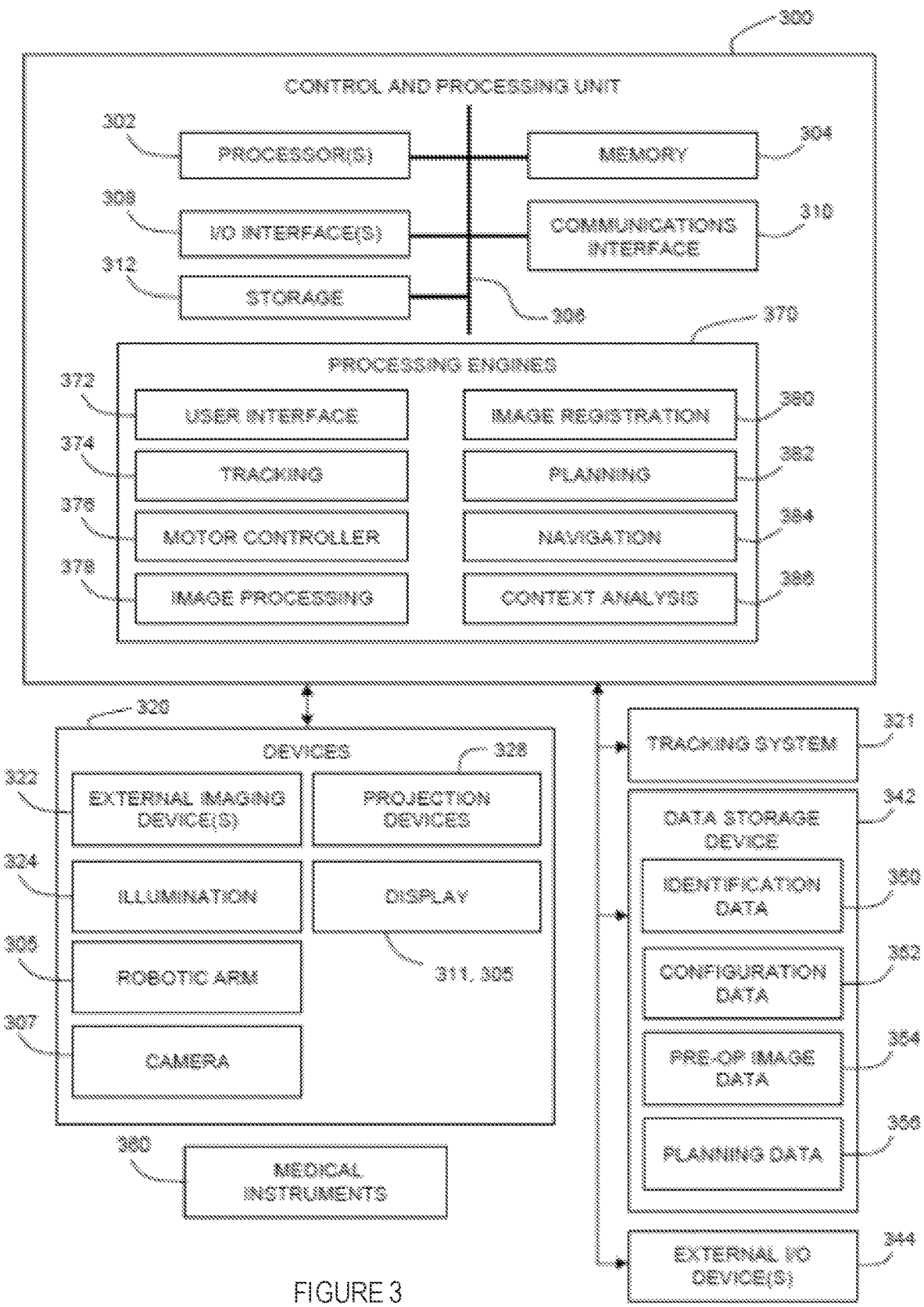
FIG. 3 is a block diagram illustrating relationships between components of a surgical navigation system, such as a control and processing unit, a tracking system, a data storage device for the tracking system, system devices, and medical instruments/tools, in accordance with an embodiment of the present disclosure.

With reference to FIG. 3, and in accordance with one embodiment, relationships between components of an overall surgical navigation system 200, such as a control and processing unit 300, a tracking system 321, a data storage device 342 for the tracking system 321, and system devices 320, and medical instruments 360, will now be described. The control and processing unit 300 comprises at least one processor 302, a memory 304, such as a non-transitory memory device, a system bus 306, at least one input/output interface 308, a communications interface 310, and storage device 312. The control and processing unit 300 is interfaced with other external devices, such as the tracking system 321, data storage 342 for the tracking system 321, and external user input and output devices 344, optionally comprising, for example, at least one of a display device, a keyboard, a mouse, a foot pedal, a microphone, and a speaker.

The data storage 342 comprises any suitable data storage device, such as a local or remote computing device, e.g. a computer, hard drive, digital media device, or server, having a database stored thereon. The data storage device 342 includes identification data 350 for identifying at least one medical instrument 360 and configuration data 352 for associating customized configuration parameters with at least one medical instrument 360. The data storage device 342 further comprises at least one of preoperative image data 354 and medical procedure planning data 356. Although data storage device 342 is shown as a single device, understood is that, in other embodiments, the data storage device 342 comprises multiple storage devices. The data storage device 342 is also configured to store data in a custom data structure corresponding to various 3D volumes at different resolutions, wherein each may be captured with a unique time-stamp and/or quality metric. This custom data structure provides the system 200 (FIGS. 1 and 2) with an ability to move through contrast, scale, and time during the surgical procedure.

Medical instruments (tools) 360 are identifiable by the control and processing unit 300, wherein the medical instruments 360 are coupled with, and controlled by, the control and processing unit 300. Alternatively, the medical instruments 360 are operable or otherwise independently employable without the control and processing unit 300. The tracking system 321 may be employed to track at least one of the medical instruments 360 and spatially register the at least one medical instrument 430 in relation to an intraoperative reference frame. As noted above, the tracking system 321 may thus furnish the requisite position, orientation and location data to associate tool/probe data with corresponding locations within the surgical cavity.

The control and processing unit 300 is also interfaceable with a number of configurable devices, and may intraoperatively reconfigure at least one such device based on configuration parameters obtained from configuration data 352. Examples of devices 320 include, but are not limited to, at least one external imaging device 322, at least one illumination device 324, robotic arm 305, at least one projection device 328, and at least one display device 311, 305.

The control and processing unit 300 is operable by the at least one processor 302 and the at least one memory 304. For example, the functionalities described herein are at least partially implemented via hardware logic in processor 302 by way of the instructions stored in memory 304 though at least one processing engine 370. Examples of processing engines 370 include, but are not limited to, user interface engine 372, tracking engine 374, motor controller 376, image processing engine 378, image registration engine 380, procedure planning engine 382, navigation engine 384, and context analysis module 386. Understood is that the system 200 (FIGS. 1 and 2) is not intended to be limited to the components shown in the several figures of the Drawing. One or more components of the control and processing 300 may be provided as an external component or device. In one alternative embodiment, navigation module 484 may be provided as an external navigation system that is integrated with control and processing unit 300.

Embodiments of the system 200 of FIG. 2 may be implemented using processor 302 without additional instructions stored in memory 304. Embodiments may also be implemented using the instructions stored in the memory 304 for execution by one or more general purpose microprocessors.

Thus, the disclosure is not limited to a specific configuration of hardware, firmware, and/or software. While some embodiments can be implemented in fully functioning computers and computer systems, various embodiments are capable of being distributed as a computing product in a variety of forms and are capable of being applied regardless of the particular type of machine or computer readable media used to actually effect the distribution. At least some aspects disclosed can be embodied, at least in part, in software. That is, the techniques may be carried out in a computer system or other data processing system in response to its processor, such as a microprocessor, executing sequences of instructions contained in a memory, such as ROM, volatile RAM, non-volatile memory, cache or a remote storage device. A computer readable storage medium can be used to store software and data which when executed by a data processing system causes the system to perform various methods. The executable software and data may be stored in various places including for example ROM, volatile RAM, nonvolatile memory and/or cache. Portions of this software and/or data may be stored in any one of these storage devices.

The preceding exemplary embodiments involve systems and methods in which a device is intra-operatively configured based on the identification of a medical instrument. In other example embodiments, one or more devices may be automatically controlled and/or configured by determining one or more context measures associated with a medical procedure. A "context measure", as used herein, refers to an identifier, data element, parameter or other form of information that pertains to the current state of a medical procedure. In one example, a context measure may describe, identify, or be associated with, the current phase or step of the medical procedure. In another example, a context measure may identity the medical procedure, or the type of medical procedure, that is being performed. In another example, a context measure may identify the presence of a tissue type during a medical procedure. In another example, a context measure may identify the presence of one or more fluids, such as biological fluids or non-biological fluids (e.g. wash fluids) during the medical procedure, and may further identify the type of fluid. Each of these examples relate to the image-based identification of information pertaining to the context of the medical procedure.

Examples of computer-readable storage media include, but are not limited to, recordable and non-recordable type media such as volatile and non-volatile memory devices, ROM, RAM, flash memory devices, floppy and other removable disks, magnetic disk storage media, optical storage media (e.g., compact discs (CDs), digital versatile disks (DVDs), etc.), among others. The instructions can be embodied in digital and analog communication links for electrical, optical, acoustical or other forms of propagated signals, such as carrier waves, infrared signals, digital signals, and the like. The storage medium may be the internet cloud, or a computer readable storage medium such as a disc.

At least some of the methods described herein are capable of being distributed in a computer program product comprising a computer readable medium that bears computer usable instructions for execution by one or more processors, to perform aspects of the methods described. The medium may be provided in various forms such as, but not limited to, one or more diskettes, compact disks, tapes, chips, USB keys, external hard drives, wire-line transmissions, satellite transmissions, internet transmissions or downloads, magnetic and electronic storage media, digital and analog signals, and the like. The computer useable instructions may also be in various forms, including compiled and non-compiled code.

While the present disclosure describes various embodiments for illustrative purposes, such description is not intended to be limited to such embodiments. On the contrary, the applicant's teachings described and illustrated herein encompass various alternatives, modifications, and equivalents, without departing from the embodiments, the general scope of which is defined in the appended claims. Except to the extent necessary or inherent in the processes themselves, no particular order to steps or stages of methods or processes described in this disclosure is intended or implied. In many cases the order of process steps may be varied without changing the purpose, effect, or import of the methods described.

Information as herein shown and described in detail is fully capable of attaining the above-described object of the present disclosure, the presently preferred embodiment of the present disclosure, and is, thus, representative of the subject matter which is broadly contemplated by the present disclosure. The scope of the present disclosure fully encompasses other embodiments which may become apparent to those skilled in the art, and is to be limited, accordingly, by nothing other than the appended claims, wherein any reference to an element being made in the singular is not intended to mean "one and only one" unless explicitly so stated, but rather "one or more." All structural and functional equivalents to the elements of the above-described preferred embodiment and additional embodiments as regarded by those of ordinary skill in the art are hereby expressly incorporated by reference and are intended to be encompassed by the present claims. Moreover, no requirement exists for a system or method to address each and every problem sought to be resolved by the present disclosure, for such to be encompassed by the present claims. Furthermore, no element, component, or method step in the present disclosure is intended to be dedicated to the public regardless of whether the element, component, or method step is explicitly recited in the claims. However, that various changes and modifications in form, material, work-piece, and fabrication material detail may be made, without departing from the spirit and scope of the present disclosure, as set forth in the appended claims, as may be apparent to those of ordinary skill in the art, are also encompassed by the disclosure.

What is claimed is:

1. A medical probe for internally probing tissue or fluid within a body, the probe comprising:
    a multichannel fiber bundle comprising a plurality of optical fibers associated with a plurality of distinct optical probe channels; and
    a common monolithic optical probe tip structure microfabricated via a 3D laser printing process, the common monolithic optical probe tip structure configured to concurrently engage and respectively optically couple the common monolithic optical probe tip structure with a common distal end of each optical fiber of the plurality of optical fibers, whereby respective preconfigured optical channel paths within the common monolithic optical probe tip structure are defined, the common monolithic optical probe tip structure comprising at least one of a micro-fabricated respective probe tip port and a respective waveguide to controllably engage and respectively optically couple the common monolithic optical probe tip structure with each optical fiber of the plurality of optical fibers, the common monolithic optical probe tip structure comprising at least one of a beam shaping element an a beam steering element, and the beam shaping element comprising at least one of a lens grating and a set of sequential lenses.

2. The medical probe of claim 1,
    wherein said illumination waveguide comprises a core illumination waveguide,
    wherein said collection waveguide comprises a set of circumferentially disposed collection waveguides circumferentially disposed around and parallel to said core illumination waveguide, and
    wherein said optical probe tip structure is optically fabricated atop and to optically couple with both said core illumination waveguide and said circumferentially disposed collection waveguides.

3. The medical probe of claim 1,
    wherein said optical response is defined by a designated optical collection spectrum, and
    wherein said optical probe tip structure further comprises a collection wavelength-selective element defined within a collection optical path of said optical response toward said collection waveguide to at least partially confine said optical response to said designated optical collection spectrum.

4. The medical probe of claim 3, wherein said collection wavelength-selective element comprises an optical coating deposited upon a surface previously fabricated within said optical path.

5. The medical probe of claim 1, wherein said optical probe tip structure comprises a monolithic structure fabricated of light-transmissive material and integrally shaped to optically couple to both said illumination waveguide and said collection waveguide and optically relay said optical illumination and optical response therefrom and thereto, respectively.

6. The medical probe of claim 1, wherein said optical probe tip structure is at least partially manufactured by a micro-optical 3D printing process executed to directly manufacture said probe tip structure atop both said optical illumination waveguide and said optical collection waveguide.

7. The medical probe of claim 1, wherein said optical probe tip structure further comprises a reflective surface for redirecting at least one of said optical illumination and said optical response.

8. The medical probe of claim 1, wherein said optical probe tip structure is at least partially fabricated to define one or more beam shaping elements.

9. The medical probe of claim 1,
    wherein the probe is a disposable probe to be operatively coupled at said external end thereof to a reusable device housing an illumination light source and an optical detector, and
    wherein coupling said external end to said reusable device automatically optically couples said light source to said illumination waveguide and said collection waveguide to said optical sensor.

10. The medical probe of claim 1, wherein a diameter of said probe tip comprises a range of up to, and including, approximately 2 mm.

11. The medical probe of claim 10, wherein a diameter of said probe tip structure comprises a range of up to, and including, approximately 1 mm.

* * * * *